(12) United States Patent
Ishioka

(10) Patent No.: US 11,357,459 B2
(45) Date of Patent: Jun. 14, 2022

(54) RADIATION IMAGING APPARATUS CONFIGURED TO RECEIVE A POWER IN A NON-CONTACT MANNER, RADIATION IMAGING SYSTEM, RADIATION IMAGING METHOD, AND COMPUTER-READABLE MEDIUM

(71) Applicant: CANON KABUSHIKI KAISHA, Tokyo (JP)

(72) Inventor: Toshiya Ishioka, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 181 days.

(21) Appl. No.: 16/601,780

(22) Filed: Oct. 15, 2019

(65) Prior Publication Data
US 2020/0041670 A1    Feb. 6, 2020

Related U.S. Application Data

(63) Continuation of application No. PCT/JP2018/015709, filed on Apr. 16, 2018.

(30) Foreign Application Priority Data

Apr. 19, 2017   (JP) .............................. JP2017-083235

(51) Int. Cl.
*A61B 6/00* (2006.01)
*G01T 1/17* (2006.01)
(Continued)

(52) U.S. Cl.
CPC .............. *A61B 6/4283* (2013.01); *A61B 6/42* (2013.01); *A61B 6/4208* (2013.01);
(Continued)

(58) Field of Classification Search
CPC ....... A61B 6/42; A61B 6/4208; A61B 6/4233; A61B 6/4266; A61B 6/4283; A61B 6/54;
(Continued)

(56) References Cited

U.S. PATENT DOCUMENTS 7,015,478 B2 * 3/2006 Yamamoto ............. A61B 6/542
                                                    250/370.08
7,561,668 B2 * 7/2009 Ohta ...................... G03B 42/04
                                                    378/102
(Continued)

FOREIGN PATENT DOCUMENTS

JP    2009-216441 A    9/2009
JP    2010-22836 A     2/2010
(Continued)

OTHER PUBLICATIONS

International Preliminary Report on Patentability dated Oct. 31, 2019, in corresponding PCT/JP2018/015709 (14 pages).

*Primary Examiner* — Allen C. Ho
(74) *Attorney, Agent, or Firm* — Venable LLP

(57) ABSTRACT

The radiation imaging apparatus according to the present invention is a radiation imaging apparatus arranged to detect radiation and receive power in a non-contact manner, the radiation imaging apparatus including a control unit configured to stop at least one of the non-contact power reception of and the non-contact power supply to the radiation imaging apparatus depending on the state of the radiation imaging apparatus.

17 Claims, 14 Drawing Sheets

(51) Int. Cl.
*G01T 1/29* (2006.01)
*G01T 1/36* (2006.01)
*H04N 5/32* (2006.01)

(52) U.S. Cl.
CPC .......... *A61B 6/4258* (2013.01); *A61B 6/4266* (2013.01); *A61B 6/486* (2013.01); *A61B 6/487* (2013.01); *A61B 6/54* (2013.01); *A61B 6/542* (2013.01); *A61B 6/545* (2013.01); *A61B 6/56* (2013.01); *A61B 6/563* (2013.01); *A61B 6/566* (2013.01); *G01T 1/17* (2013.01); *G01T 1/2992* (2013.01); *G01T 1/362* (2013.01); *A61B 6/485* (2013.01); *H04N 5/32* (2013.01)

(58) Field of Classification Search
CPC ........... A61B 6/542; A61B 6/545; A61B 6/56; A61B 6/563; A61B 6/566; A61B 6/4258; A61B 6/486; A61B 6/487
USPC ................ 378/62, 98.8, 189, 42; 250/370.09
See application file for complete search history.

(56) References Cited

U.S. PATENT DOCUMENTS

| | | | | |
|---|---|---|---|---|
| 7,622,889 B2* | 11/2009 | Spahn | ................... | G03B 42/02 320/101 |
| 7,696,722 B2* | 4/2010 | Utschig | ................. | G03B 42/04 320/114 |
| 7,712,959 B2* | 5/2010 | Tanabe | .................... | H01J 31/49 378/189 |
| 7,732,779 B2* | 6/2010 | Kito | ......................... | G01T 7/00 250/370.09 |
| 7,737,427 B2* | 6/2010 | Kito | ..................... | A61B 6/5282 250/580 |
| 7,772,560 B2* | 8/2010 | Ohta | ........................ | A61B 6/56 250/370.09 |
| 7,777,193 B2* | 8/2010 | Kito | ......................... | G01T 7/00 250/370.09 |
| 7,826,586 B2* | 11/2010 | Nakayama | .............. | A61B 6/56 378/101 |
| 7,847,277 B2* | 12/2010 | Kito | ......................... | A61B 6/00 250/580 |
| 7,852,985 B2* | 12/2010 | Liu | ...................... | A61B 6/4283 378/98.8 |
| 7,864,923 B2* | 1/2011 | Ohta | ...................... | G03B 42/04 378/102 |
| 7,873,145 B2* | 1/2011 | Liu | ........................ | G03B 42/02 378/98.8 |
| 7,956,330 B2 | 6/2011 | Nishino | | |
| 7,991,119 B2* | 8/2011 | Yoshida | .................... | G01T 1/00 378/114 |
| 8,053,738 B2* | 11/2011 | Nishino | ............... | A61B 6/4233 250/370.09 |
| 8,071,952 B2* | 12/2011 | Nishino | ................. | G03B 42/04 250/370.09 |
| 8,080,802 B2* | 12/2011 | Nishino | .................... | G01T 1/17 250/370.08 |
| 8,149,990 B2* | 4/2012 | De Godzinsky | ....... | A61B 6/145 378/38 |
| 8,193,509 B2 | 6/2012 | Niekawa et al. | | |
| 8,193,762 B2 | 6/2012 | Liu et al. | | |
| 8,229,202 B2* | 7/2012 | Kito | ....................... | A61B 6/542 382/132 |
| 8,324,585 B2* | 12/2012 | McBroom | ............ | G03B 42/047 250/370.09 |
| 8,334,516 B2* | 12/2012 | Tsubota | ............... | A61B 6/4283 250/370.08 |
| 8,357,908 B2* | 1/2013 | Kuwabara | .............. | A61B 6/542 250/370.08 |
| 8,399,846 B2* | 3/2013 | Niekawa | .............. | A61B 6/4283 250/370.08 |
| 8,447,011 B2* | 5/2013 | Ohta | .................... | A61B 6/4007 378/97 |
| 8,461,544 B2* | 6/2013 | Iwakiri | .................. | G03B 42/04 250/370.09 |
| 8,543,069 B2* | 9/2013 | Kari | ..................... | A61B 6/4494 455/74.1 |
| 8,546,777 B2* | 10/2013 | Utsunomiya | ........... | A61B 6/56 250/580 |
| 8,550,709 B2* | 10/2013 | Nishino | ............... | A61B 6/4476 378/207 |
| 8,586,934 B2* | 11/2013 | Nakatsugawa | ....... | G01T 1/2985 250/370.08 |
| 8,611,501 B2* | 12/2013 | Kobayashi | ................ | G01T 1/17 378/115 |
| 8,675,624 B2* | 3/2014 | Tachikawa | ............. | A61B 6/563 370/341 |
| 8,721,176 B2* | 5/2014 | McBroom | ................ | A61B 6/56 378/189 |
| 8,729,484 B2* | 5/2014 | Nishino | ................. | A61B 6/542 250/370.09 |
| 8,767,919 B2* | 7/2014 | Nishino | ............... | A61B 6/4007 378/108 |
| 8,796,623 B2* | 8/2014 | Nakatsugawa | ........... | G01T 1/20 250/336.1 |
| 8,798,235 B2* | 8/2014 | Ohta | .................... | A61B 6/4494 378/102 |
| 8,798,236 B2* | 8/2014 | Ohta | ........................ | H05G 1/10 378/102 |
| 8,861,678 B2* | 10/2014 | Liu | .......................... | H05G 1/08 378/91 |
| 8,867,702 B2* | 10/2014 | Nishino | ............... | A61B 6/4007 378/63 |
| 8,891,733 B2* | 11/2014 | Liu | ...................... | A61B 6/4405 378/91 |
| 8,929,510 B2* | 1/2015 | Nishino | ............... | A61B 6/4494 378/62 |
| 9,044,191 B2* | 6/2015 | Nishino | .................... | H05G 1/10 |
| 9,078,624 B2* | 7/2015 | Sugizaki | ............... | G01T 1/2928 |
| 9,101,316 B2* | 8/2015 | Liu | ...................... | A61B 6/4233 |
| 9,168,016 B2* | 10/2015 | Ohta | .................... | A61B 6/4283 |
| 9,258,497 B2* | 2/2016 | Tsuji | .................... | A61B 6/4233 |
| 9,259,201 B2* | 2/2016 | Sato | ........................ | A61B 6/542 |
| 9,265,476 B2* | 2/2016 | Iwakiri | ................ | A61B 6/4283 |
| 9,668,331 B2* | 5/2017 | Takahashi | ................ | H04N 5/32 |
| 9,757,089 B2* | 9/2017 | Reichel | ..................... | A61B 6/56 |
| 9,921,319 B2 | 3/2018 | Asai et al. | ............. | G01T 1/175 |
| 10,052,071 B2 | 8/2018 | Ishioka et al. | ........ | A61B 5/7405 |
| 10,238,347 B2 | 3/2019 | Ishioka et al. | ........ | A61B 5/7405 |
| 2010/0019720 A1 | 1/2010 | Liu et al. | | |
| 2010/0044572 A1 | 2/2010 | Nishino | | |
| 2010/0148085 A1 | 6/2010 | Yoshida et al. | | |
| 2011/0147601 A1 | 6/2011 | Niekawa et al. | | |
| 2011/0188630 A1 | 8/2011 | Ohta et al. | | |
| 2012/0300413 A1 | 11/2012 | Iida | | |
| 2017/0031035 A1 | 2/2017 | Ishioka | ................... | G01T 1/208 |
| 2018/0180751 A1 | 6/2018 | Asai et al. | ............. | G01T 7/005 |

FOREIGN PATENT DOCUMENTS

| | | |
|---|---|---|
| JP | 2010-158515 A | 7/2010 |
| JP | 2012-239657 A | 12/2012 |
| JP | 2012-239814 A | 12/2012 |
| JP | 2016-38341 A | 3/2016 |
| WO | 2010/021165 A1 | 2/2010 |

* cited by examiner

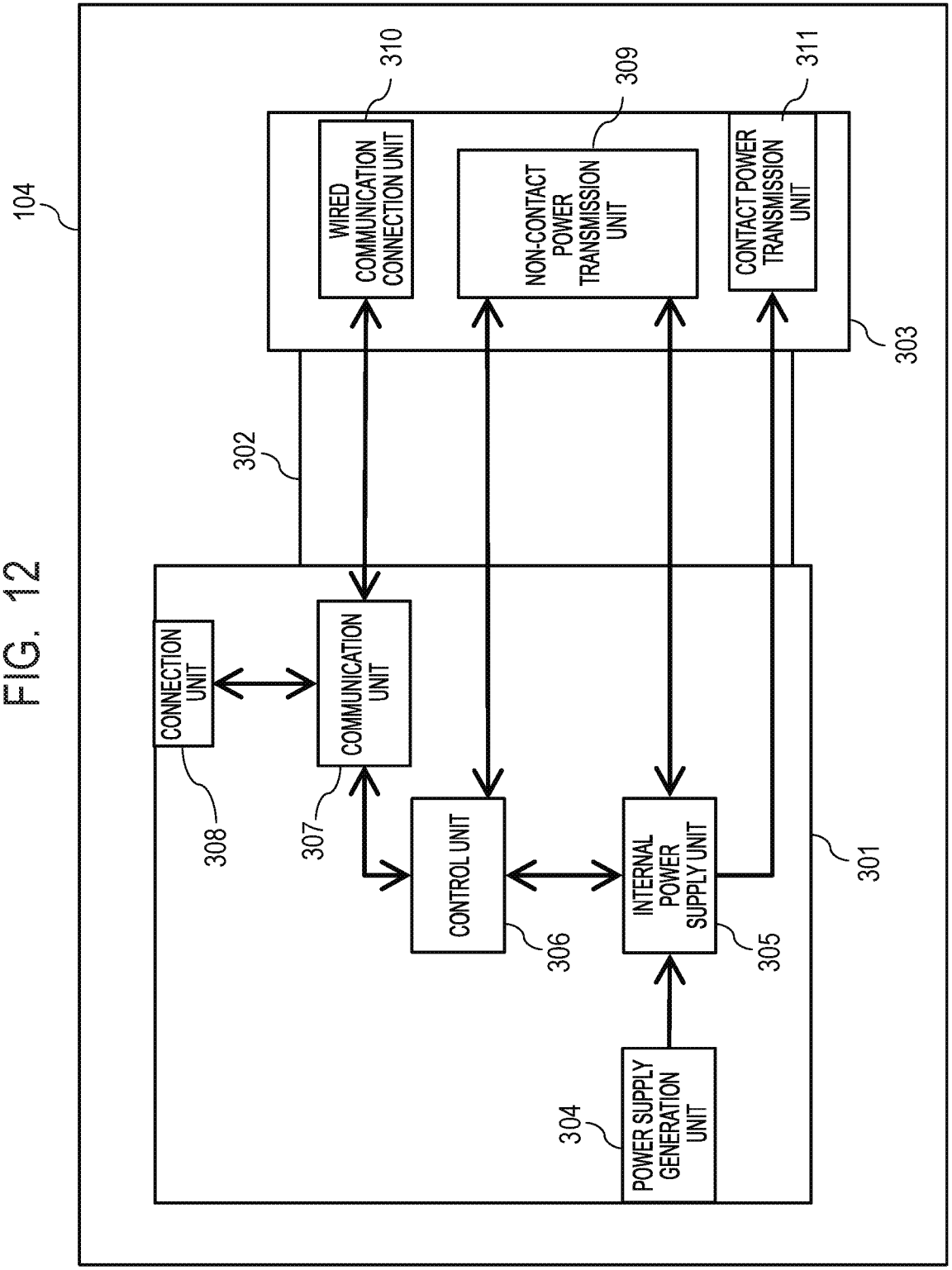

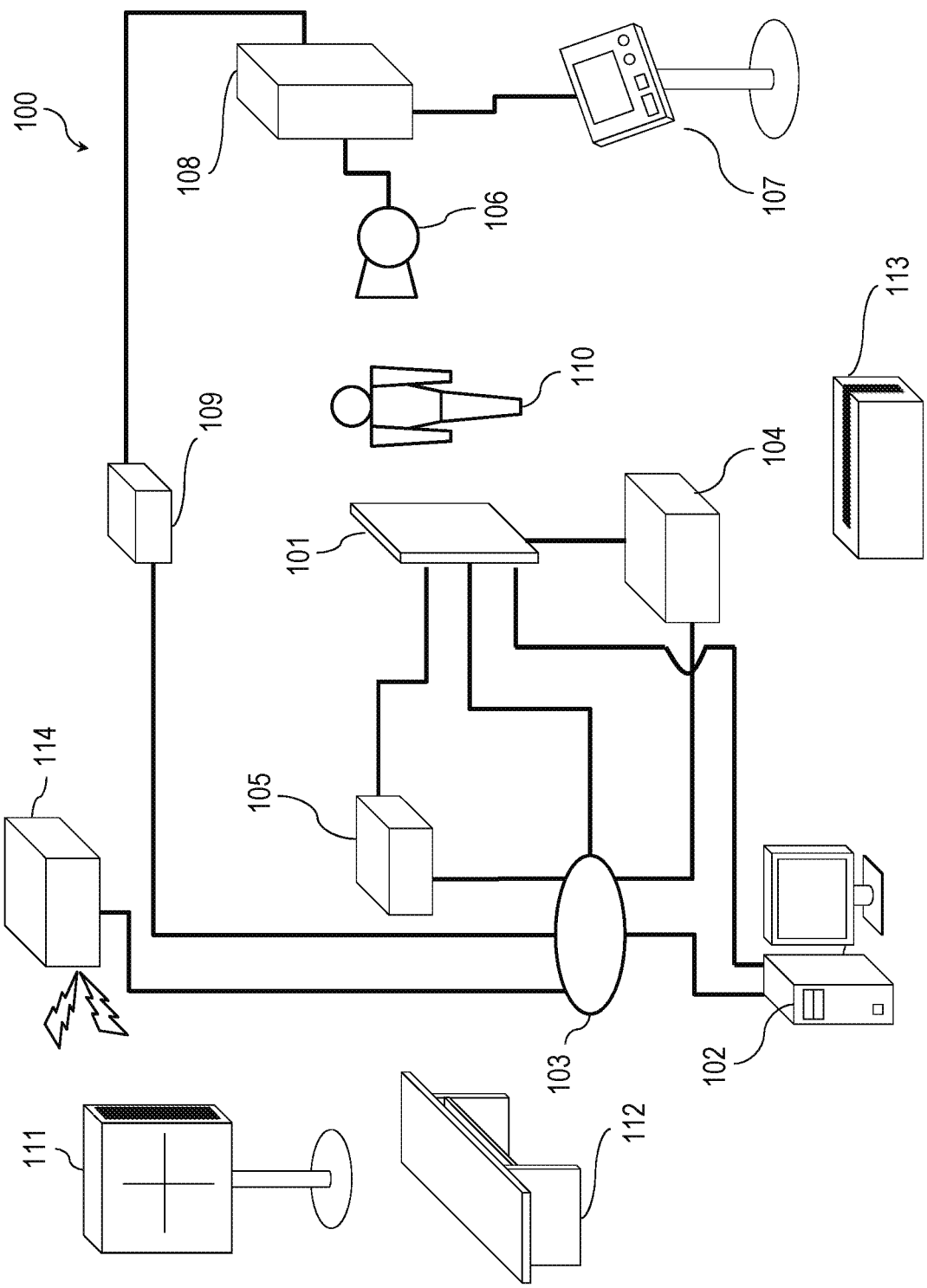

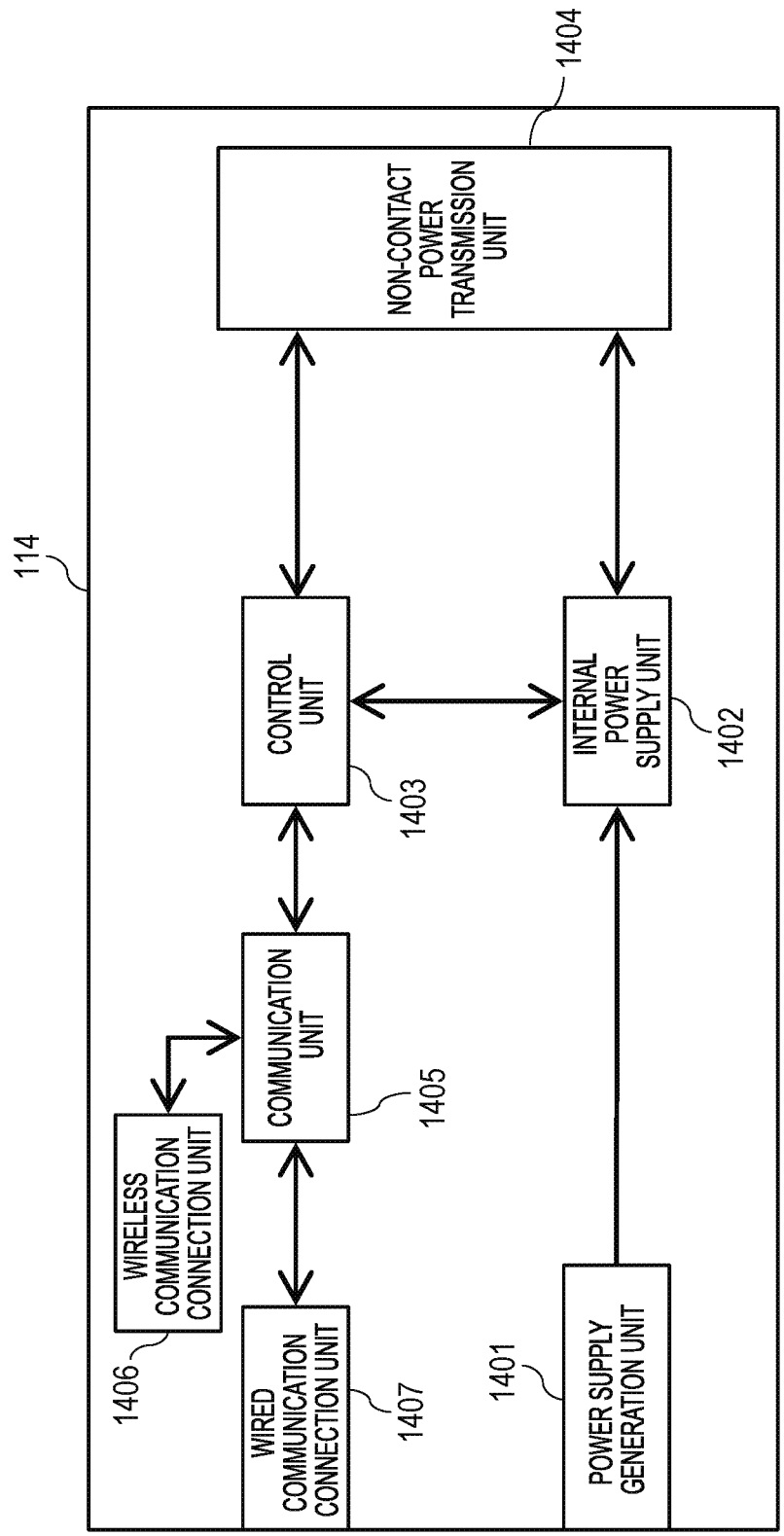

RADIATION IMAGING APPARATUS CONFIGURED TO RECEIVE A POWER IN A NON-CONTACT MANNER, RADIATION IMAGING SYSTEM, RADIATION IMAGING METHOD, AND COMPUTER-READABLE MEDIUM

CROSS-REFERENCE TO RELATED APPLICATIONS

This application is a Continuation of International Patent Application No. PCT/JP2018/015709, filed Apr. 16, 2018, which claims the benefit of Japanese Patent Application No. 2017-083235, filed Apr. 19, 2017, both of which are hereby incorporated by reference herein in their entirety.

BACKGROUND OF THE INVENTION

Field of the Invention

The present invention relates to a radiation imaging apparatus, a radiation imaging system, a radiation imaging method, and a computer-readable medium.

Description of the Related Art

Hitherto, there has been commercialized a radiation imaging apparatus irradiates an object with radiation emitted from a radiation source and detects an intensity distribution of the radiation that has been transmitted through the object to convert the intensity distribution to an image, or a radiation imaging system including the radiation imaging apparatus.

As a method of obtaining an image by the radiation imaging apparatus, there have been known a method involving using a dedicated film, and a method involving converting the radiation into visible rays by a fluorescent material and then converting the visible rays into electrical signals by an optical sensor to output the electrical signals as digital data.

The above-mentioned method of obtaining an image includes a form in which a radiation imaging apparatus arranged to use an electrical method receives power required for operation from one or both of an internal power source and an external power source to operate. Further, the case in which power is received from the external power source includes a case of using contact power supply, in which power is received through contact of a connector or other conductive members provided as a supply path on a surface of a radiation imaging apparatus main body, and a case of using non-contact power supply, in which power is received through a change in electromagnetic field from the outside.

The radiation imaging apparatus may include at least a power receiving mechanism by means of non-contact power supply as a power supply path from the outside. In the related art, power supply from the power supply path to the radiation imaging apparatus is operated by power supply processing and power supply control from outside the radiation imaging apparatus, and the radiation imaging apparatus merely receives the power supply processing and the power supply control. Specifically, there is known a form in which, when a power supply mechanism from the outside starts power transmission, the power receiving mechanism on the radiation imaging apparatus side detects the power transmission and starts receiving power. There is also a form in which, when the radiation imaging apparatus is set in a unit including a power transmission mechanism, the unit on the power transmission side detects the setting and starts power transmission.

Therefore, non-contact power supply is selected in a form in which the state of the radiation imaging apparatus is not considered, and there is a possibility of adversely affecting the operation of the radiation imaging apparatus as a result.

For example, it can be considered that, when the non-contact power supply is performed while a part incorporated in the radiation imaging apparatus is in operation, the part may be adversely affected.

SUMMARY OF THE INVENTION

According to one embodiment of the present invention, there is provided a radiation imaging apparatus arranged to detect radiation and receive power in a non-contact manner, the radiation imaging apparatus including a control unit configured to stop at least one of non-contact power reception of and non-contact power supply to the radiation imaging apparatus depending on a state of the radiation imaging apparatus.

Further features of the present invention will become apparent from the following description of exemplary embodiments with reference to the attached drawings.

BRIEF DESCRIPTION OF THE DRAWINGS

FIG. 12 is a diagram for illustrating a configuration example of a power supply unit in the second embodiment.

FIG. 13 is a diagram for illustrating a configuration example of a radiation imaging system according to a fourth embodiment of the present invention.

FIG. 14 is a diagram for illustrating a configuration example of a non-contact power supply unit.

DESCRIPTION OF THE EMBODIMENTS

Embodiments of the present invention will be described below in detail with reference to the accompanying drawings.

First Embodiment

Figure 1:
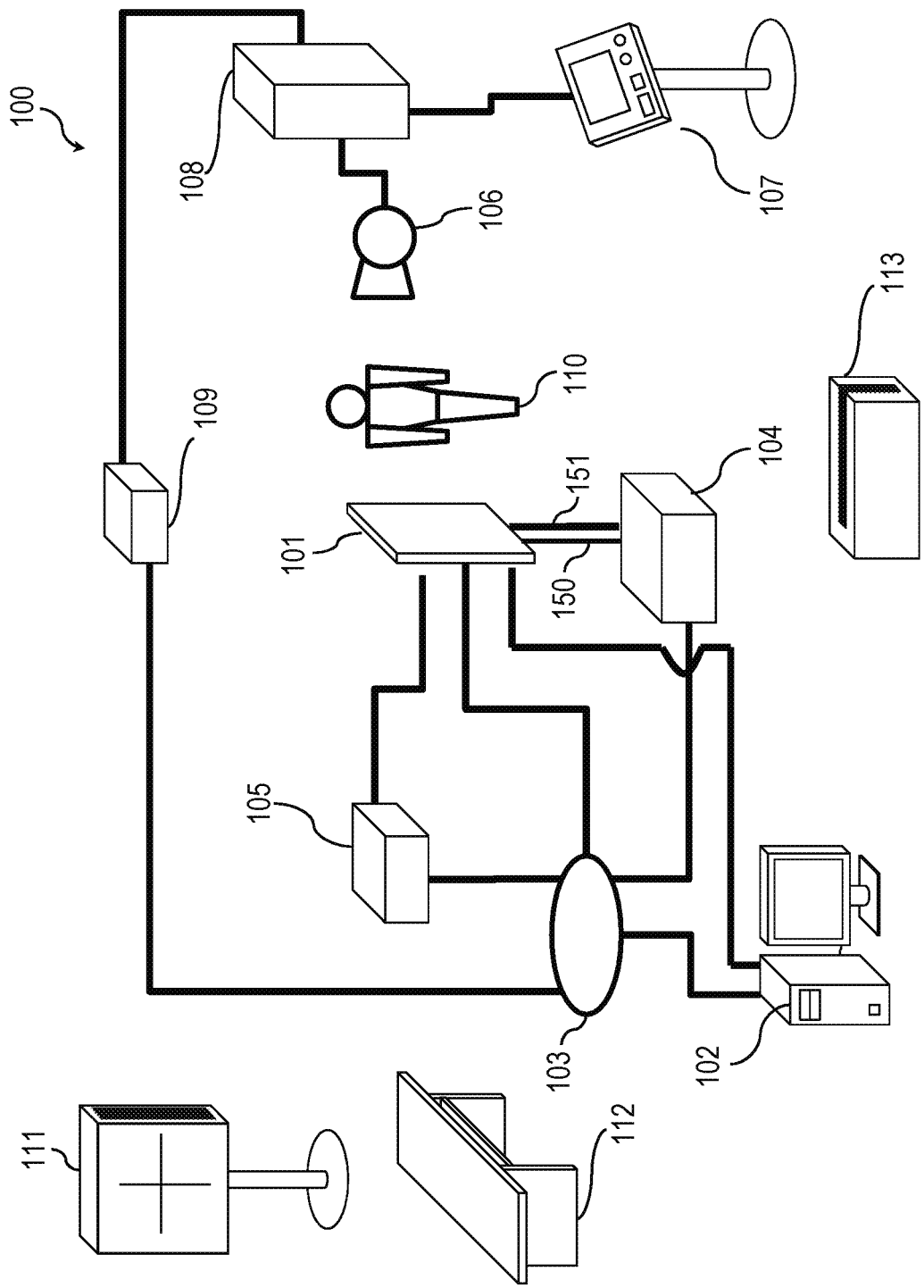
FIG. 1 is a block diagram a diagram for illustrating a configuration example of a radiation imaging system according to a first embodiment of the present invention.

In a first embodiment of the present invention, there is described an example in which a radiation imaging apparatus 101 includes a non-contact power receiving mechanism, and when it is determined to be required, an instruction for stopping power transmission is issued to a power transmission side to stop transmission and reception of power by means of non-contact power supply. In FIG. 1, there is illustrated a configuration example of a part of a radiation imaging system 100 including the radiation imaging apparatus 101 according to the first embodiment. Now, components of the radiation imaging system 100 and a relationship thereof are described with reference to FIG. 1.

The radiation imaging apparatus 101 has at least a wired communication function or a wireless communication function, or both of the communication functions to transmit and receive data to and from a console 102 through a communication path. The console 102 is formed of a PC including a monitor or other display functions and a function of an input from a user to notify the radiation imaging apparatus 101 of the instruction from the user, and receive an image acquired by the radiation imaging apparatus 101 and present the image to the user.

The console 102 also has a wired communication function or a wireless communication function, or both of the communication functions. In FIG. 1, the console 102 of a stationary type is illustrated. However, there is no particular restriction thereon in actual operation, and the console 102 may be a notebook PC or tablet device of a portable type, for example.

When the radiation imaging apparatus 101 acquires an image, image data is transmitted to the console 102 via a configuration of any one of constituent elements 103 to 105 of the communication path, or the image data is directly transmitted to the console 102 depending on a configuration status of the system.

For example, the constituent element 103 is a communication network (for example, LAN network), and the radiation imaging apparatus 101 and the console 102 are connected to the communication network 103 through a wired cable to transmit and receive data.

The radiation imaging apparatus 101 also has at least a non-contact power receiving function, and when the radiation imaging apparatus 101 is brought close to a power supply unit 104 which supplies power, the power supply unit 104 is allowed to supply power to the radiation imaging apparatus 101. In a case where the radiation imaging apparatus 101 further has a non-contact proximity communication function, when the non-contact power receiving function and a proximity unit are provided in the same portion, power reception and communication can be performed by the radiation imaging apparatus 101 being brought close to the power supply unit 104.

In FIG. 1, of lines connecting the radiation imaging apparatus 101 and the power supply unit 104, a line 150 means a wiring for communication, and a line 151 means contact for power supply. In FIG. 1, there is illustrated a form in which the power supply unit 104 is connected to the communication network 103, but there may be adopted a form in which the power supply unit 104 and the console 102 are directly and electrically connected to each other.

When the radiation imaging apparatus 101 has the wireless communication function, transmission and reception of data to and from the console 102 may be achieved via an access point 105 (hereinafter referred to as "AP 105"). In FIG. 1, there is illustrated a form in which the AP 105 is connected to the communication network 103, but as in the case of the power supply unit 104, the AP 105 may be directly and electrically connected to the console 102.

Further, when the radiation imaging apparatus 101 and the console 102 have functions of directly transmitting and receiving data to and from each other, the data may be directly transmitted and received wirelessly or via wire.

An example of the path through which the data is transmitted and received between the radiation imaging apparatus 101 and the console 102 has been described above.

Now, a cradle 113 being a charger for the radiation imaging apparatus 101 is described. Although an internal configuration of the radiation imaging apparatus 101 is to be described later, the radiation imaging apparatus 101 includes an internal power source, for example, a battery, and the internal power source can be charged by externally supplying power to the radiation imaging apparatus 101. Although the internal power source can be charged also by receiving power from the power supply unit 104 described above, the cradle 113 is prepared as a device on which the radiation imaging apparatus 101 is mounted when imaging through radiation irradiation is not performed or in other cases to charge the internal power source.

The cradle 113 at least has installed therein a non-contact power supply mechanism, and when the radiation imaging apparatus 101 is mounted thereon, detects the mounting to enter a state in which the power supply can be started. As a result, the radiation imaging apparatus 101 can receive power and charge the internal power source.

In FIG. 1, the cradle 113 is illustrated as existing alone. It should be noted, however, that a plurality of cradles 113 may each have a communication function to connect to each device via the communication network 103 to enable communication between the radiation imaging apparatus 101 and each device when the radiation imaging apparatus 101 is mounted on the cradle 113.

Next, an outline of imaging of an object 110 by radiation is described. Here, processing in a synchronous imaging mode, in which imaging is performed in synchronization with radiation irradiation of a radiation generating apparatus 108, is described.

In imaging the object 110, the radiation imaging apparatus 101 is placed at a position at which radiation that has been emitted from a radiation tube (radiation generating unit) 106 and transmitted through the object 110 is received.

To describe an example of an imaging flow, after an operator starts the radiation imaging apparatus 101, a person taking an image operates the console 102 to set the radiation imaging apparatus 101 to a state in which an image can be taken. Subsequently, the person taking an image operates a radiation generating apparatus console 107 to set conditions on the radiation with which to irradiate. After the above-mentioned processing is finished, the person taking an image confirms that preparations for imaging including the object 110 are made, and presses an exposure switch included in the radiation generating apparatus console 107 to perform exposure with the radiation.

Upon the exposure with the radiation, the radiation generating apparatus 108 notifies the radiation imaging apparatus 101 of a signal indicating that the irradiation with the radiation is to be performed, via a connector 109 and the communication network 103. In FIG. 1, the radiation generating apparatus 108 and the radiation imaging apparatus 101 are connected to each other via the connector 109 and the communication network 103, but the connection is not limited to that form. Depending on the functions of the radiation imaging apparatus 101, the notification of the irradiation may not be required as described later.

When the signal indicating that the irradiation with the radiation is to be performed reaches the radiation imaging apparatus 101, the radiation imaging apparatus 101 checks whether a state thereof is ready for radiation irradiation, and responds to the radiation generating apparatus 108 with permission for irradiation when there is no problem. As a result, the irradiation with the radiation is performed.

When detecting the end of the radiation irradiation by various methods, such as a notification from the radiation generating apparatus 108 or referring to a set time determined in advance, the radiation imaging apparatus 101 starts generating an image, and generated image data is transmitted to the console 102 through the above-mentioned communication path. The data transmitted to the console 102 can be displayed on a display unit included in the console 102.

The radiation imaging apparatus 101 is incorporated in a rack 111 or a bed 112 for imaging depending on conditions, such as a site to be imaged and a condition of the object, to take an image.

The operation in the synchronous imaging mode has been described above.

Further, when the radiation imaging apparatus 101 includes a radiation irradiation detecting mode, the imaging flow is changed. In the radiation irradiation detecting mode, after the radiation imaging apparatus 101 is set to a state in which radiation irradiation can be detected, the radiation imaging apparatus 101 is irradiated with the radiation at a given timing. When the radiation imaging apparatus 101 detects the radiation irradiation, processing for acquiring the image is started. Therefore, transmission and reception relating to the permission for radiation irradiation between the radiation generating apparatus 108 and the radiation imaging apparatus 101 is not required in the processing.

Figure 2:
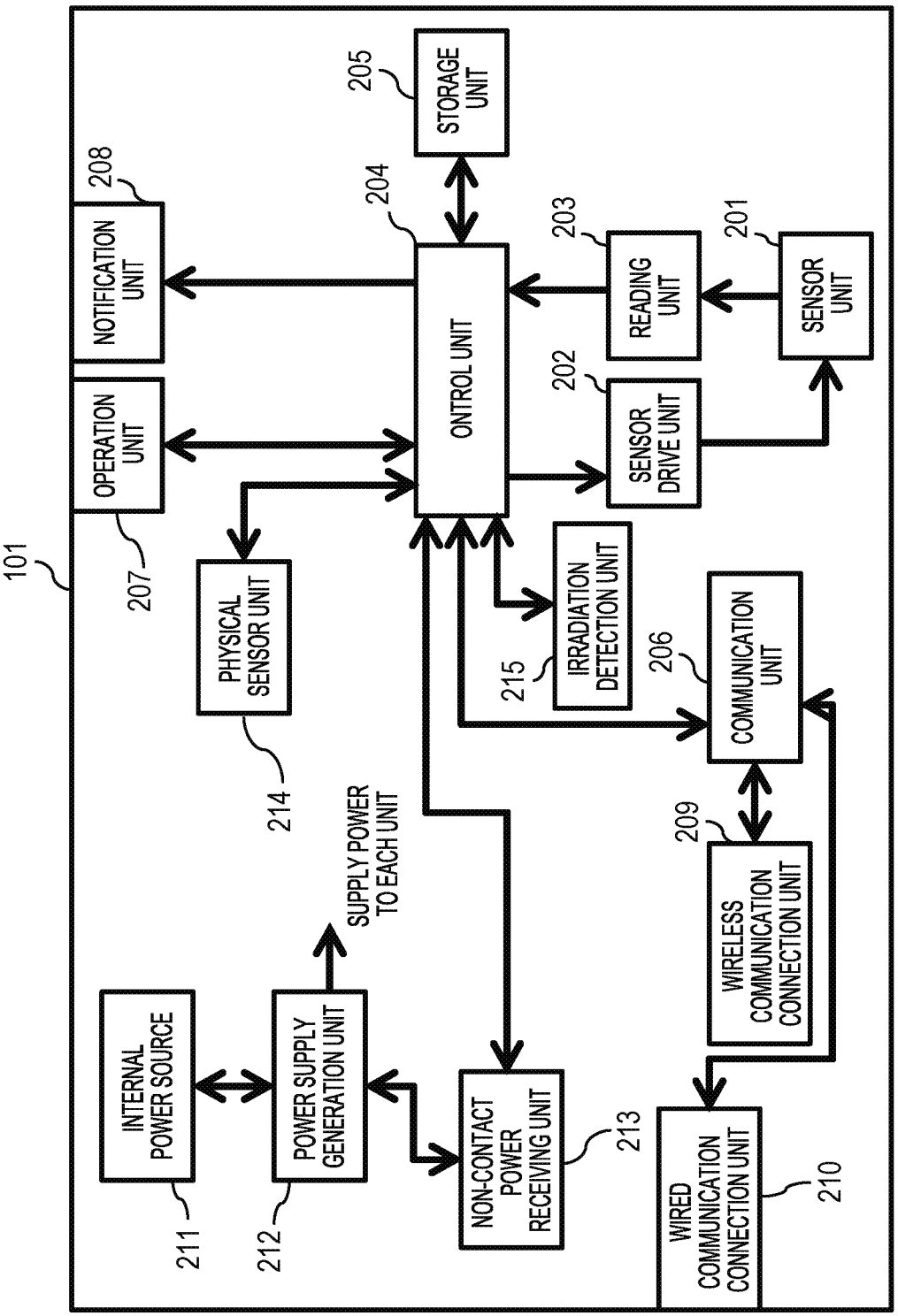
FIG. 2 is a diagram for illustrating a configuration example of a radiation imaging apparatus according to the first embodiment.

Next, the radiation imaging apparatus 101 is described with reference to FIG. 2.

The radiation imaging apparatus 101 includes a sensor unit 201 which converts incident radiation into electrical signals. The sensor unit 201 is further formed of a scintillator and a photodetector array. The scintillator and the photodetector array each have a shape of a two-dimensional plane, and are adjacent to each other in a manner in which surfaces thereof face each other.

The scintillator is excited by X-rays and other radiations to emit visible rays, and electric charges corresponding to intensities and periods of the light are accumulated in pixels of the photodetector array.

A sensor drive unit 202 is configured to drive the above-mentioned sensor unit 201 which detects the radiation as the electric charges, and a reading unit 203 which receives the electric charges output as a result of driving the sensor unit 201, and convert the electric charges into digital information. When extracting the accumulated electric charges, the sensor drive unit 202 selects from which row or column of the photodetector array to extract the electric charges, and the reading unit 203 amplifies and then digitizes the extracted electric charges.

Data obtained by the digitization by the reading unit 203 is sent to a control unit 204, and is sent by the control unit 204 to a storage unit 205. The image data stored in the storage unit 205 is sent to an external device via a functional unit relating to communication, or is sent to an external device after the control unit 204 performs some processing thereon. Further, the image data may be directly stored in the storage unit 205 in some cases.

As a configuration of the sensor unit 201, various configurations can be considered without any particular limitation on a type of the scintillator and a type of a photodetector, the control unit 204, or the storage unit 205.

The control unit 204 performs processing regarding control of each unit of the radiation imaging apparatus 101. For example, the control unit 204 outputs an instruction to drive the sensor unit 201 for imaging to the sensor drive unit 202, and stores and extracts the obtained image data in and from the storage unit 205.

The control unit 204 is further configured to transmit the image data to another device via a communication unit 206, receive an instruction similarly via the communication unit 206, or switch start/stop of the radiation imaging apparatus 101 by an operation from an operation unit 207, for example. Further, the control unit 204 is also capable of notifying the user of an operation status or an error condition via a notification unit 208. In the first embodiment, the above-mentioned processing details are processed by the control unit 204, but a plurality of control units 204 may be included to process the above-mentioned processing details in a distributed manner. Further, in terms of specific implementation, the control unit 204 is not particularly limited, and may be implemented by a CPU, an MPU, an FPGA, a CPLD, and other various devices.

The storage unit 205 is used to store log information indicating the image acquired by the radiation imaging apparatus 101 and results of internal processing, for example. When the control unit 204 is a CPU or other devices using software, the storage unit 205 may also store software for that purpose, for example.

There is no restriction on specific implementation, and the storage unit 205 may be mounted in various combinations of a memory, an HDD, and volatile/non-volatile memories. Further, only one storage unit 205 is illustrated in the first embodiment, but a plurality of storage units 205 may be provided.

The communication unit 206 performs processing for achieving communication between the radiation imaging apparatus 101 and other devices. The communication unit 206 in the first embodiment is connected to a wireless communication connection unit 209 for wireless communication to communicate to/from the AP 105 and the console 102 via the wireless communication connection unit 209. An example of the wireless communication connection unit 209 is an antenna for wireless communication.

The communication unit 206 is also connected to a wired communication connection unit 210 to communicate to/from the console 102 via the wired communication connection unit 210. In FIG. 2, the wired communication connection unit 210 is in contact with the exterior of the radiation imaging apparatus 101, and may be connected thereto via a connector or short-range non-contact communication. In the first embodiment, a short-range non-contact communication function is described to be incorporated in configurations of the units including the power supply unit 104 to be described later as an example.

The communication unit 206 is not limited to the above-mentioned form, and there may be employed a configuration in which only a wired communication function or a wireless communication function is included. Further, communication standard and method are not particularly limited.

The radiation imaging apparatus 101 includes an internal power source 211. In the first embodiment, the internal power source 211 is a rechargeable battery, and is in a removable form. The internal power source 211 is not limited to this example, and may take various combinations of a rechargeable form, a non-rechargeable form, a removable form, a non-removable form, and a power generation method, for example.

A power supply generation unit 212 generates, distributes, and supplies a voltage and an electric current required by the units of the radiation imaging apparatus 101 based on the power supplied from the internal power source 211. Further, when being brought close to a member which performs a non-contact power supply function of the power supply unit 104, the radiation imaging apparatus 101 can receive the power supplied from the power supply unit 104 with the use of a non-contact power receiving unit (power receiver) 213. This power is used to supply power to each unit of the radiation imaging apparatus 101, and charge the internal power source 211. The non-contact power receiving unit 213 can start non-contact power reception by being brought closer to the power supply unit 104 which performs the non-contact power supply.

The non-contact power receiving unit 213 may not only receive power, but also transmit and receive information on the non-contact power supply between the power transmission side and the power receiving side with the use of a communication function incorporated in the same power receiving mechanism or the same part or unit as the power receiving mechanism. In other words, the non-contact power receiving unit 213 may transmit and receive the information to and from the power supply unit 104.

In the first embodiment, proximity communication can be performed to and from the power transmission side with the use of the same part (for example, coil). Therefore, in FIG. 2, the non-contact power receiving unit 213 and the control unit 204 are connected to each other. The non-contact power receiving unit 213 and the control unit 204 may transmit and receive the information to and from each other in between transmission and reception regarding the communication with the use of the communication unit 206 or a dedicated communication unit that is newly provided.

The operation unit 207 is used to receive an operation from the user. An implementation method thereof is not particularly limited as long as an input from the user can be received. Specifically, the operation unit 207 may be implemented as various switches and a touch panel manually operated by the user. The operation unit 207 may also include a receiving unit which receives an input from a remote controller dedicated for operations.

The notification unit 208 is used to notify the user, for example, of the state of the radiation imaging apparatus 101, for example. An implementation method thereof is not particularly limited, and may be implemented by an LED, an LCD, a monitor, and other devices. Further, as a method of notifying the user, a speaker or other sound generating functions may be provided.

A physical sensor unit 214 is a sensor unit detects various physical events. Examples of physical phenomena include a temperature, acceleration, geomagnetism, and an electromagnetic field. The control unit 204 determines the status of the radiation imaging apparatus 101 depending on detected information of the physical events to notify an alarm when a high temperature or a strong impact is received, or to determine an orientation of its installation and the like and transmit information for increasing usability to the user or the console 102.

An irradiation detection unit 215 has a function of detecting whether irradiation with radiation is performed. As an implementation method of the irradiation detection unit 215, as with the sensor unit 201, there are a plurality of implementation methods including a method of detecting with the use of a scintillator and an optical sensor, and a method of detecting a flow of an electric current generated in the sensor unit 201 by the radiation irradiation. In the first embodiment, a method using an electrical mechanism is considered.

In other words, any method is considered as long as the detection method includes a mechanism using a voltage or an electric current (electric charges), for example. Therefore, in FIG. 2, the irradiation detection unit 215 is described as a single functional unit, but may be integrated with the sensor unit 201 or other units.

When detecting that irradiation with the radiation is performed, the irradiation detection unit 215 notifies the control unit 204 of the irradiation. When receiving the notification, the control unit 204 controls the sensor unit 201, the sensor drive unit 202, and the reading unit 203 to accumulate the electric charges generated by the radiation in the sensor unit 201 and read the electric charges to generate an image as in the synchronous mode.

Figure 3:
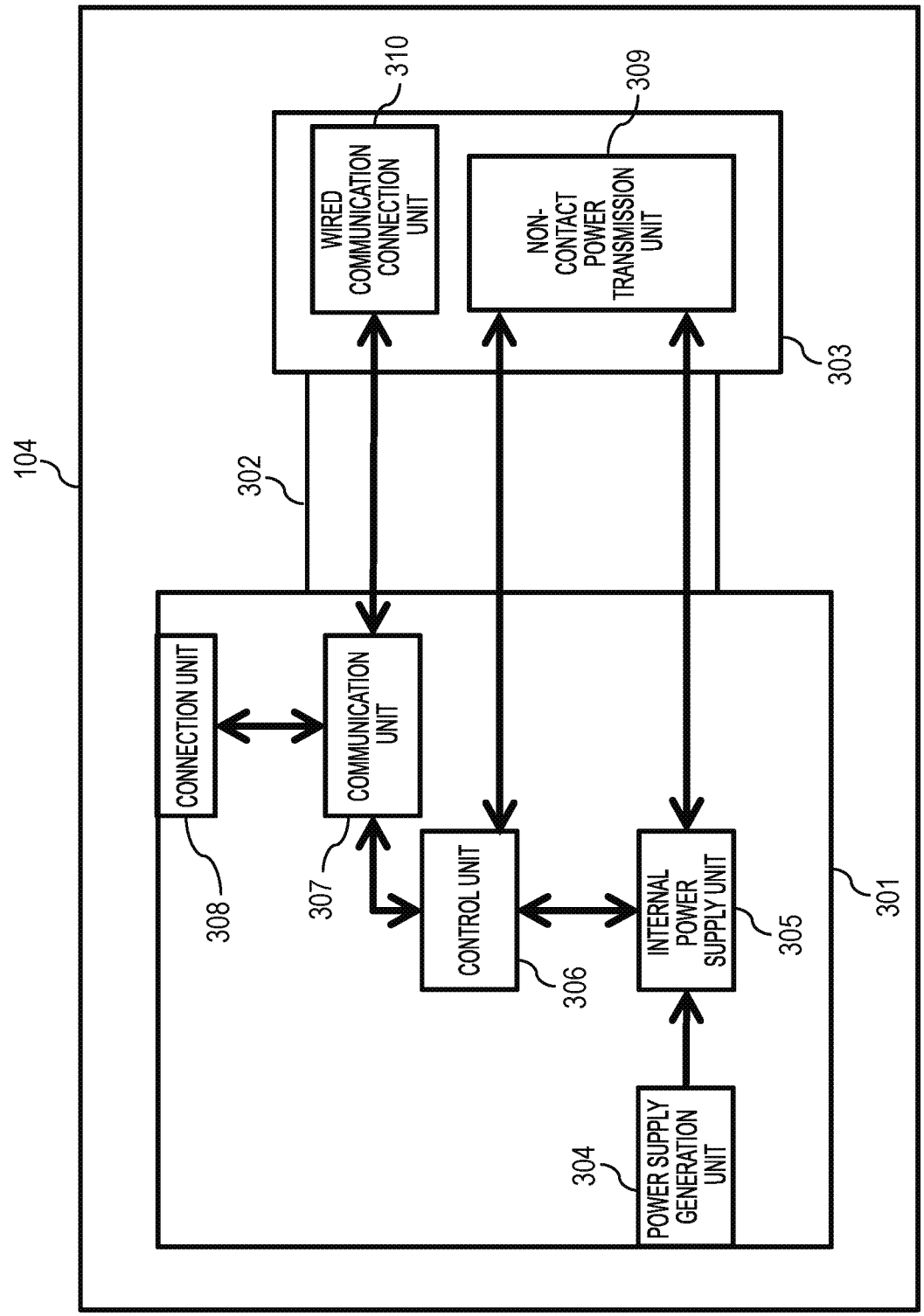
FIG. 3 is a diagram for illustrating a configuration example of a power supply unit in the first embodiment.

Next, a configuration of the power supply unit 104 is described. In FIG. 3, a configuration example of the power supply unit 104 is illustrated. The power supply unit (power supply) 104 in the first embodiment includes a power supply unit main body 301, a power supply unit cable 302, and a power supply unit proximity portion 303.

When power is to be supplied to the radiation imaging apparatus 101, the power supply unit proximity portion 303 is brought close to, or into contact with, the power receiving unit of the radiation imaging apparatus 101, and the power supply unit main body 301 can be placed in a place away from the radiation imaging apparatus 101 through the power supply unit cable 302. The "contact" as used herein refers to bringing the exteriors into contact with each other.

The power supply unit main body 301 includes a power supply generation unit 304 which receives power from an AC power source and convert the power into a DC voltage, and an internal power supply unit 305 which generates power to be used by each unit in the power supply unit 104. The power supply unit main body 301 also includes a control unit 306 which controls each unit, a communication unit 307 which performs communication between the power supply unit 104 and another unit, and a connection unit 308, which is a connection unit for communication to/from a device other than the radiation imaging apparatus 101.

The power supply unit proximity portion 303 includes a non-contact power transmission unit 309 and a wired communication connection unit 310. The non-contact power transmission unit 309 receives power for transmission from the internal power supply unit 305, and is controlled for power transmission by the control unit 306. The non-contact power transmission unit 309 is also configured to perform communication regarding the non-contact power supply with the use of the same part as with the non-contact power receiving unit 213 of the radiation imaging apparatus 101 in the first embodiment.

The wired communication connection unit 310 is a part paired with the wired communication connection unit 210 in the radiation imaging apparatus 101 described above. As described above, the wired communication connection unit 210 in the first embodiment assumes short-range wireless communication, and hence the corresponding wired communication connection unit 310 of the power supply unit 104 also has a similar configuration and function. It should be noted, however, that the part relating to communication may be implemented by communication by contact, such as using a connector.

In order to perform the communication, the wired communication connection unit 310 is connected to the communication unit 307 through the power supply unit cable 302.

The case in which the power supply unit main body 301 and the power supply unit proximity portion 303 are placed at separate places through the cable has been assumed, but the power supply unit proximity portion 303 may be implemented in a form of being incorporated in the main body.

Figure 4:
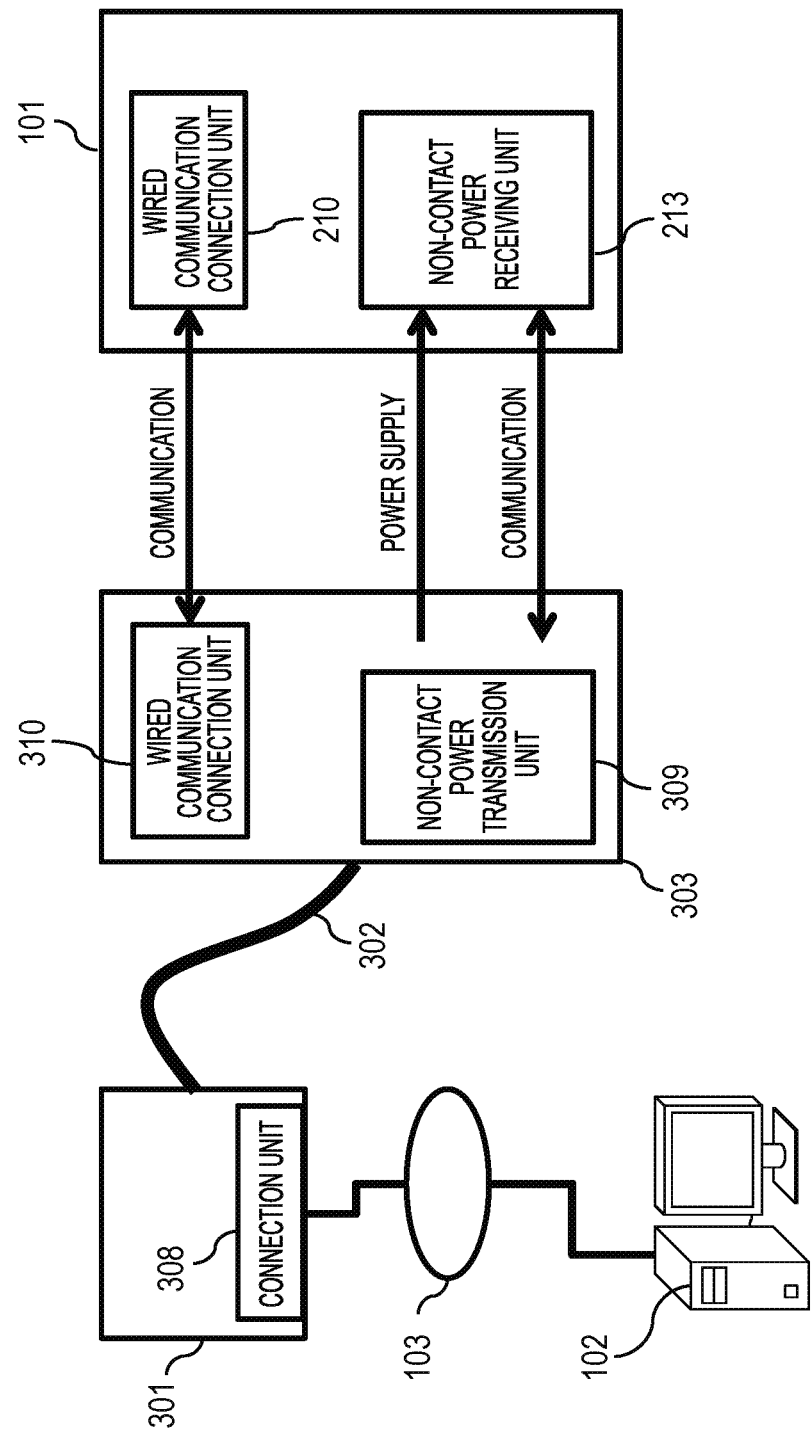
FIG. 4 is a diagram for illustrating an example of communication and power supply between the power supply unit and the radiation imaging apparatus.

The configurations of the radiation imaging apparatus 101 and the power supply unit 104 have been described, and FIG. 4 is a schematic diagram of a connection configuration described in the first embodiment as an example of the connection. In FIG. 4, an example of how connections are established from the radiation imaging apparatus 101 to the console 102 and what kind of information is communicated is illustrated based on FIG. 1 to FIG. 3.

Attention is focused here on the part relating to the non-contact power supply involving the power supply unit 104 and wired connection communication (proximity non-contact communication), and hence a communication path and a connection form by means of wireless communication are not to be mentioned. In FIG. 4, power transmission and information transmission are also illustrated.

When the radiation imaging apparatus 101 receives power from the power supply unit 104, the power supply unit proximity portion 303 is brought close to the radiation imaging apparatus 101 in advance. For stabilization of arrangement, the exteriors of the housings may be brought into contact with each other. Under this state, communication for recognizing each other is performed between the non-contact power transmission unit and the non-contact power receiving unit via coils for transmitting and receiving power, and when it is determined that power transmission can be performed, power is supplied from the non-contact power transmission unit 309, and the power is received by the non-contact power receiving unit 213 and used in the radiation imaging apparatus 101.

When the image acquired by the radiation imaging apparatus 101 is to be transferred to an external device, data is transmitted and received with the use of the wired communication connection units 210 and 310. When the image acquired by the radiation imaging apparatus 101 is to be transferred to the console 102, the image is transmitted from the radiation imaging apparatus 101 to the console 102 by means of the connection units 210 and 310 via the communication unit 307 and the connection unit 308 of the power supply unit 104, and the communication network 103.

As has been repeatedly described, the connections are merely an example. Therefore, the wired communication connection unit may employ a method by means of contact via a connector, or the communication relating to the non-contact power supply may be achieved with the use of another path, for example.

Next, a configuration example of the cradle 113 is described.

Figure 5:
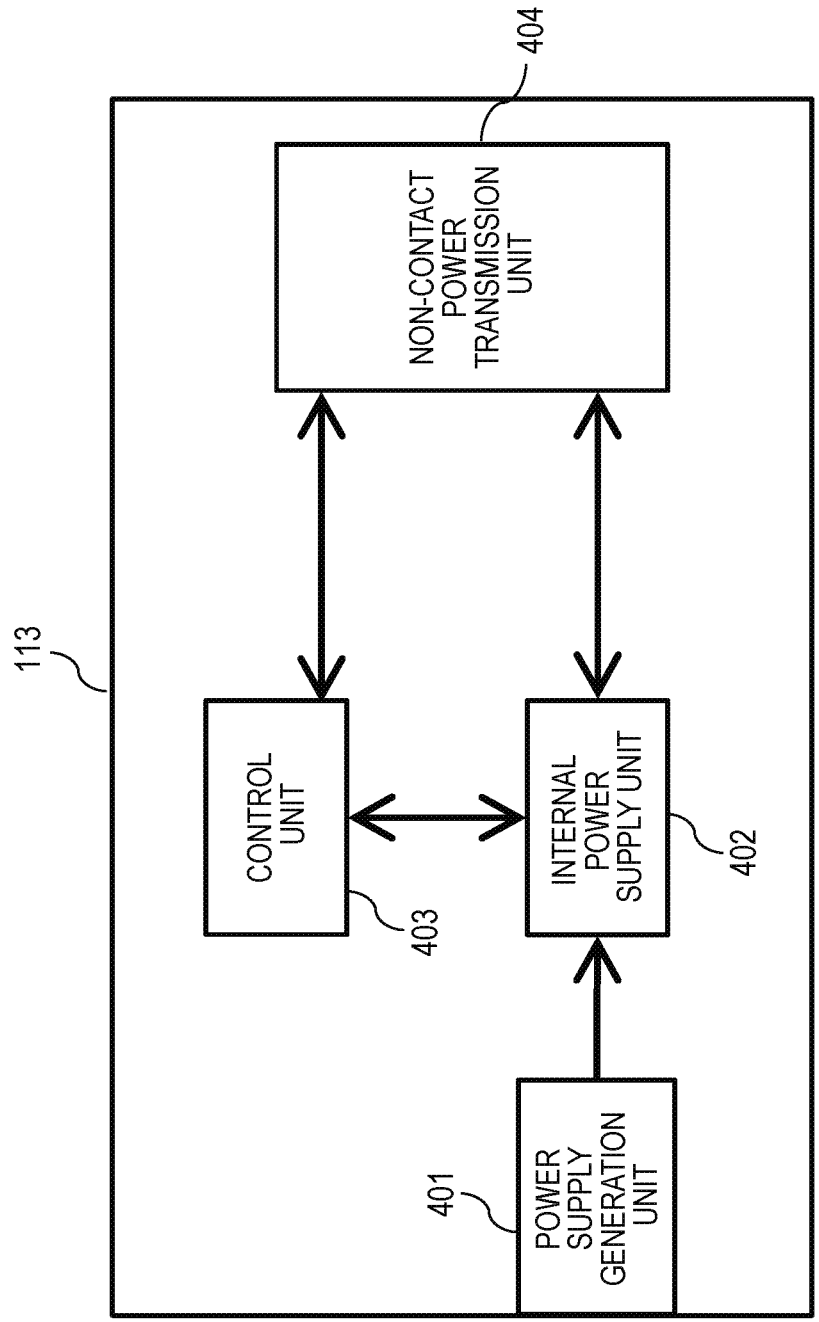
FIG. 5 is a diagram for illustrating a configuration example of a cradle.

The cradle 113 is used when the radiation imaging apparatus 101 is to be charged as described above. Therefore, a basic configuration thereof is as illustrated in FIG. 5. Specifically, the cradle 113 includes a power supply generation unit 401 which receives power from an AC power source and convert the power into a DC voltage, an internal power supply unit 402 which generates power to be used by each unit in the cradle 113, a control unit 403 which controls each unit, and a non-contact power transmission unit 404.

An outline of processing of supplying power to the radiation imaging apparatus 101 is similar to that of the power supply unit 104, and hence a description thereof is omitted. As has been described in the description of FIG. 1, a mechanism configured to enable communication between the radiation imaging apparatus 101 and another unit may be provided in the cradle 113.

For the rack 111 and the bed 112, when the power supply unit proximity portion 303 is arranged in advance in a place in which the radiation imaging apparatus 101 is to be accommodated, and when the radiation imaging apparatus 101 is mounted, the non-contact power supply can be performed as in the case where the radiation imaging apparatus 101 is connected to the power supply unit 104. As a simple example, a set of the power supply unit 104 may be mounted to the rack 111. Further, for the shape of the power supply unit 104, a form via a cable as illustrated in FIG. 3 or a form in which the proximity unit and the main body are integrated with each other may be adopted.

Based on the above description, a case in which the non-contact power supply is performed in practice and processing of stopping the power supply are described. The radiation imaging apparatus 101 of the first embodiment, which detects radiation and receive power in a non-contact manner, includes the control unit 204 for stopping at least one of non-contact power reception of and non-contact power supply to the radiation imaging apparatus 101 depending on a state of the radiation imaging apparatus 101. For example, the control unit 204 stops at least one of the non-contact power reception of and the non-contact power supply to the radiation imaging apparatus 101 when the radiation imaging apparatus 101 is in a state in which the radiation is detectable.

In the first embodiment, situations of stopping power supply include "image read period", "in the radiation irradiation detecting mode", and "in detection operations of various physical sensors". Each situation is described below.

Figure 6:
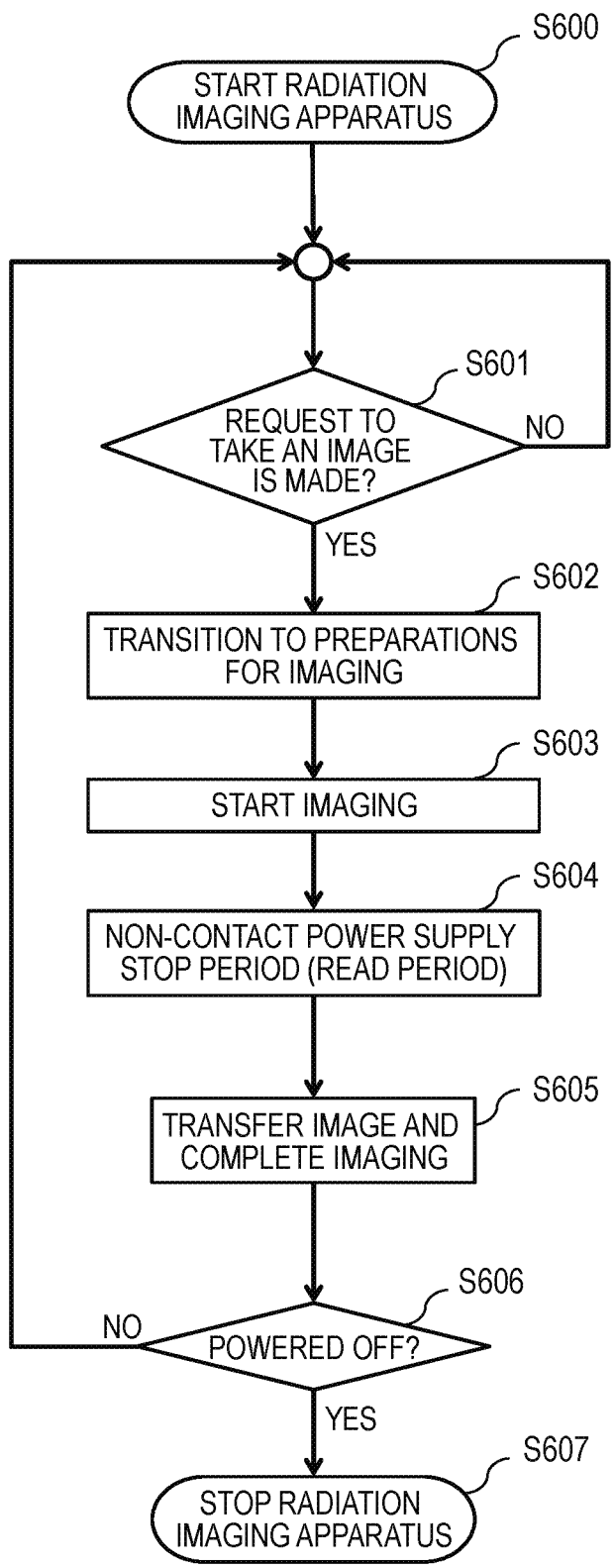
FIG. 6 is a flow chart for illustrating processing of a synchronous imaging mode.

First, as an example of the processing of stopping the non-contact power supply, the "image read period" is described. In FIG. 6, a basic flow in the synchronous imaging mode is illustrated.

When the radiation imaging apparatus 101 is started, power is supplied to each required functional units, and the functional units starts operating. It is not required that the functional units to be started be all functional units in the radiation imaging apparatus 101. For example, functional units for use in imaging, such as the sensor unit 201, may not be started until a request to take an image is made.

Subsequently, the processing proceeds to Step S601, in which it is determined whether a request to take an image is made from the radiation generating apparatus 108. When a request is not made, a request to take an image is waited for continuously. When a request is made, the processing proceeds to Step S602, and the processing proceeds to preparations for imaging. After the preparations for imaging are performed, the processing proceeds to Step S603, in which imaging is started. Thereafter, the processing proceeds to Step S604, in which the image is read. After the image is read in Step S604, the radiation imaging apparatus 101 transfers the read image to the outside (for example, console 102) in Step S605 and completes imaging. Thereafter, it is determined whether the radiation imaging apparatus 101 is powered off in Step S606. When the radiation imaging apparatus 101 is not powered off, the processing is returned to Step S601, and when the radiation imaging apparatus 101 is powered off, the radiation imaging apparatus 101 is caused to stop operating in Step S607.

Here, there is a period of stopping the non-contact power supply while the radiation imaging apparatus 101 sequentially performs the transitions to the preparations for imaging to the completion of the imaging. The period of stopping the power supply is the "image read period" in the first embodiment.

To be specific, the "image read period" is a period for the sensor drive unit 202 to select a read line to extract the electric charges accumulated in the sensor unit 201, and for the reading unit 203 to capture and digitize the electric charges. The image is read line by line, and hence time until reading is complete for all the lines set to be read is the image read period. When the radiation imaging apparatus 101 is in a state of reading the electric charges from the sensor unit 201, the control unit 204 stops at least one of the non-contact power reception and the non-contact power supply.

While a radiation image of the object 110 is taken, the radiation imaging apparatus 101 is in a state of acquiring an image by irradiation being performed with radiation from the radiation generating apparatus 108 which generates the radiation, and the control unit 204 stops at least one of the non-contact power reception and the non-contact power supply.

Some radiation imaging apparatus 101 acquire a total of two images: an image of offset information of a sensor array and an image after the radiation irradiation, to generate one image. In that case, read periods for acquiring the images are the "image read period". While the image of offset information is taken, the radiation imaging apparatus 101 is in a state of acquiring an image without irradiation with radiation from the radiation generating apparatus 108 which generates the radiation, and the control unit 204 stops at least one of the non-contact power reception of and the non-contact power supply to the radiation imaging apparatus 101.

This period is a period of extracting a minute amount of electric charges required for generating an image, and when the non-contact power supply is not performed in this period, electromagnetic noise is prevented from generating an induced electromotive force and an electric current generated thereby on the sensor array to affect the image. In the period of stopping the power supply, the radiation imaging apparatus 101 operates on power from the internal power source. Therefore, when there is no sufficient remaining power in the internal power source, there may be adopted a form in which the user is warned by notification of the remaining power, or a form in which it is prevented to transition to an imaging operation.

Next, processing of actually stopping and restarting the power supply is described as an example. At a timing at which the processing in the image taking proceeds to Step S604, the radiation imaging apparatus 101 issues a notification to stop power transmission to the power supply unit 104 as a power supply side. The control unit 204 transmits, to the power supply unit (power supply unit) 104 which performs the non-contact power supply to the radiation imaging apparatus 101, information on stopping the non-contact power supply.

In the first embodiment, the non-contact power transmission unit 309 and the non-contact power receiving unit 213 have a communication function with which the information on the power supply can be transmitted and received, and hence the control unit 204 of the radiation imaging apparatus 101 issues the instruction to stop the power supply via the non-contact power receiving unit 213. The instruction received by the non-contact power transmission unit 309 from the non-contact power receiving unit 213 is received by the control unit 306 of the power supply unit 104, and in response to the instruction to stop the power transmission, the control unit 306 instructs the internal power supply unit 305 to stop supplying power to the non-contact power transmission unit, to thereby stop the power transmission.

A flow in restarting the power transmission is similar to the above, and when the "image read period" is ended, the radiation imaging apparatus 101 issues a notification of permitting restart of power supply along the same transmission path as that in stopping the power supply, and the power supply unit 104 side also restarts power supply from the non-contact power transmission unit in the same manner. The control unit 204 transmits, to the power supply unit (power supply) 104 which performs the non-contact power supply to the radiation imaging apparatus 101, information on the start of the non-contact power supply.

Here, the information has been transmitted and received with the use of the non-contact power transmission unit 309 and the non-contact power receiving unit 213, but the information may be communicated with the use of the wired communication connection units 210 and 310, the wireless communication connection unit 209, and the AP 105.

Next, as an example of the processing of stopping the non-contact power supply, "in the radiation irradiation detecting mode" is described.

Now, the radiation irradiation detecting mode and a radiation irradiation detection function are described again. As described above, the radiation irradiation detection function is a function in which the radiation imaging apparatus 101 itself determines whether the radiation irradiation is performed, and when it is determined that the irradiation with the radiation is performed, the electric charges caused by the radiation are accumulated in the sensor unit 201, and then read as an image. The sensor unit 201 detects the radiation irradiation from the radiation generating apparatus 108 which generates the radiation.

The radiation irradiation detecting mode is a mode in which the image is acquired by the radiation irradiation detection function described above. In the radiation irradiation detecting mode, the notification on the radiation irradiation is not communicated between the radiation generating apparatus 108 and the radiation imaging apparatus 101, and the connector 109 illustrated in FIG. 1 is not required.

Figure 7:
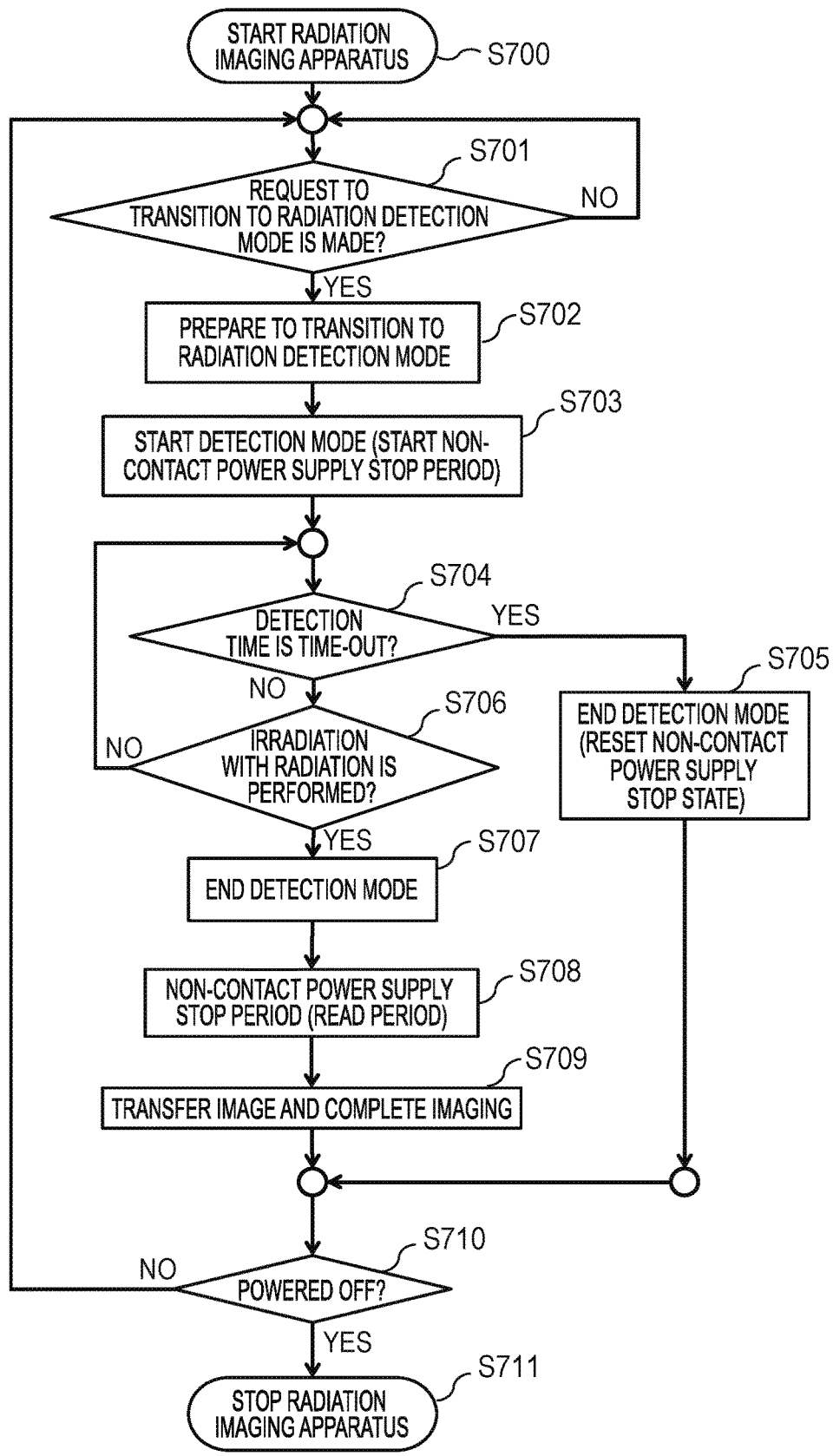
FIG. 7 is a flow chart for illustrating processing of a radiation irradiation detecting mode.

In FIG. 7, a basic flow in the radiation irradiation detecting mode is illustrated. Processing immediately after the radiation imaging apparatus 101 is started is the same as the flow of FIG. 6 during the synchronous imaging. That is, power is supplied to each required functional units, and the functional units starts operating. It is not required that the functional units to be started be all functional units in the radiation imaging apparatus 101. For example, functional units for use in imaging, such as the sensor unit 201, may not be started until a request to take an image is made.

Subsequently, the processing proceeds to Step S701, in which it is determined whether a request to transition to imaging in the radiation irradiation detecting mode is made, and when the request is made, the processing proceeds to Step S702. In the first embodiment, imaging in the radiation irradiation detecting mode is assumed, but there may be adopted a configuration in which switching is made between the synchronous imaging mode and the radiation irradiation detecting mode as described above, and processing of making the determination may be performed before Step S701.

As an example, the request to transition to the irradiation detection mode may be issued as an instruction to start an imaging sequence from the console 102 corresponding to the radiation imaging apparatus 101.

In Step S702, processing of preparing, for example, energizing and starting the functional units, for transitioning to the radiation irradiation detecting mode is performed. Thereafter, the processing proceeds to Step S703, in which transitions are actually made to a state of waiting for irradiation with the radiation and, at the same time, to a non-contact power supply stopping period. When the sensor unit 201 (radiation imaging apparatus 101) is in a state in which the radiation irradiation is detectable, the control unit 204 stops at least one of the non-contact power reception of and the non-contact power supply to the radiation imaging apparatus 101.

Processing of stopping and restarting the power supply is the same as the processing performed when the non-contact power supply is stopped during the "image read period" described above.

In Step S704, it is determined whether detection time is time-out. Depending on the radiation detection method, the detection waiting time may be set to unlimited, but when actual use is considered, it is preferred to stop the processing after predetermined time to prepare for a case of being left without any radiation irradiation.

Further, for a detection method in which the detection time is limited, a form in which time-out time is set is appropriate. When it is determined as a result of the processing of Step S704 that irradiation waiting time has reached the time-out time, the processing proceeds to Step S705, in which the radiation detection mode is ended. As a result, the non-contact power supply can be restarted, and processing of restarting is similar to the above-mentioned processing performed when the "image read period" is ended and the power supply is restarted.

Meanwhile, when it is determined in Step S704 that the time-out time has not elapsed, the processing proceeds to Step S706 in which it is determined whether irradiation with the radiation is performed. When it is determined in Step 706 that the irradiation is not performed, the processing returns to Step S704, and the processing loop is repeated until the detection time is time-out while the non-contact power supply is stopped or the irradiation with the radiation is performed.

When it is determined in Step S706 that the irradiation with the radiation is performed, the processing proceeds to Step S707, in which the radiation detection mode is ended.

Thereafter, the processing proceeds to Step S708, in which, in order to accumulate the electric charges to form an image by the radiation with which the irradiation is being performed, the sensor unit 201 is set to a state in which the electric charges can be accumulated until the irradiation with the radiation is finished. The processing of Step S707 is described because the sensor unit 201 used for acquiring the image is also used as a detection unit for detecting the radiation in this description, but when the sensor unit 201 is not used as the detection unit, the sensor unit 201 may be set in advance to the state in which the electric charges can be accumulated.

Subsequently, after the irradiation with the radiation is finished, as in the synchronous imaging, an image is read, and when the reading is complete, the processing proceeds to Step S709. When the imaging is completed in Step S709, the processing proceeds to Step S710, and it is determined whether the radiation imaging apparatus 101 is powered off in Step S710. When the radiation imaging apparatus 101 is not powered off, the processing is returned to Step S701, and when the radiation imaging apparatus 101 is powered off, the operation of the radiation imaging apparatus 101 is stopped in Step S711.

The non-contact power supply can be restarted when the processing proceeds to Step S709, and processing to be performed at that time is similar to the above-mentioned returning method.

In the first embodiment, the non-contact power supply is stopped continuously after the start of the radiation detection mode until the reading in Step S708. It should be noted, however, that in a case where there is some time from when the radiation irradiation is detected and the detection mode is ended in Step S707 to when the reading in Step S708 is started, or in a case where the function affected by the change in magnetic field is not in operation, the non-contact power supply may be returned for that period.

Next, as an example of the processing of stopping the non-contact power supply, "in the physical sensor detecting mode" is described.

As described with reference to FIG. 2, the radiation imaging apparatus 101 includes the physical sensor unit 214 which detects the predetermined physical quantity of the radiation imaging apparatus 101. When the non-contact power supply is performed in the vicinity at the timing when the physical sensor unit 214 is operated, an error may be caused in output data of the sensor. When the physical sensor unit 214 is in the state in which the physical quantity is detectable, the control unit 204 stops at least one of the non-contact power reception of and the non-contact power supply to the radiation imaging apparatus 101.

For example, a temperature sensor which detects a temperature of the radiation imaging apparatus 101 is provided, and detects heat generated in the radiation imaging apparatus 101 by the operation of the radiation imaging apparatus 101 itself, and monitors and provides warning so that the temperature does not reach a predetermined temperature or more. When the change in electromagnetic field caused by the non-contact power supply affects the output of the temperature sensor under this state, the warning about an increased temperature is output to the console 102 or other devices although the temperature is not increased, and there is a possibility that the imaging cannot be performed.

To address this problem, when the temperature sensor is in the state in which the temperature of the radiation imaging apparatus 101 is detectable, the control unit 204 stops at least one of the non-contact power reception of and the non-contact power supply to the radiation imaging apparatus 101.

A geomagnetic sensor which detects posture of the radiation imaging apparatus 101 and an acceleration sensor which detects acceleration of the radiation imaging apparatus 101 may also be provided. In this case, the radiation imaging apparatus 101 detects the orientation of its installation and the like with the use of the geomagnetic sensor and the acceleration sensor to determine, in conjunction with the console 102, in which orientation the acquired image is to be displayed on the console 102 and display the acquired image. When those sensors are affected by the change in electromagnetic field caused by the non-contact power supply, there is a possibility that the display is not performed in a suitable manner.

To address this problem, when the geomagnetic sensor or the acceleration sensor is in the state in which the posture or the acceleration of the radiation imaging apparatus 101 is detectable, the control unit 204 stops at least one of the non-contact power reception of and the non-contact power supply to the radiation imaging apparatus 101.

Further, some sensors require calibration before the start of the operation, and when the sensors are affected by the electromagnetic field during the calibration, reference numerical values may become erroneous.

In order to prevent the above-mentioned situation, a method involving stopping the non-contact power supply in the period in which the sensors operate can be considered. Accordingly, when the physical sensor unit 214 is in the state of being calibrated, the control unit 204 stops at least one of the non-contact power reception of and the non-contact power supply to the radiation imaging apparatus 101.

As a timing of stopping, the control unit 204 of the radiation imaging apparatus 101 may stop the non-contact power supply before the physical sensor unit 214 is operated, and may return the non-contact power supply after the physical sensor unit 214 stops operating.

As an example, a case in which the temperature sensor is operated is described. It is assumed that, instead of outputting the temperature detection result at all times, the temperature sensor responds when the control unit 204 makes an inquiry. In this case, the temperature may be measured at intervals of predetermined time to correspond to a rate of temperature change that is presumed in practice. As a specific example, when the presumed temperature change can be sufficiently tracked by measurement per minute, the temperature may be measured every minute.

Figure 8:
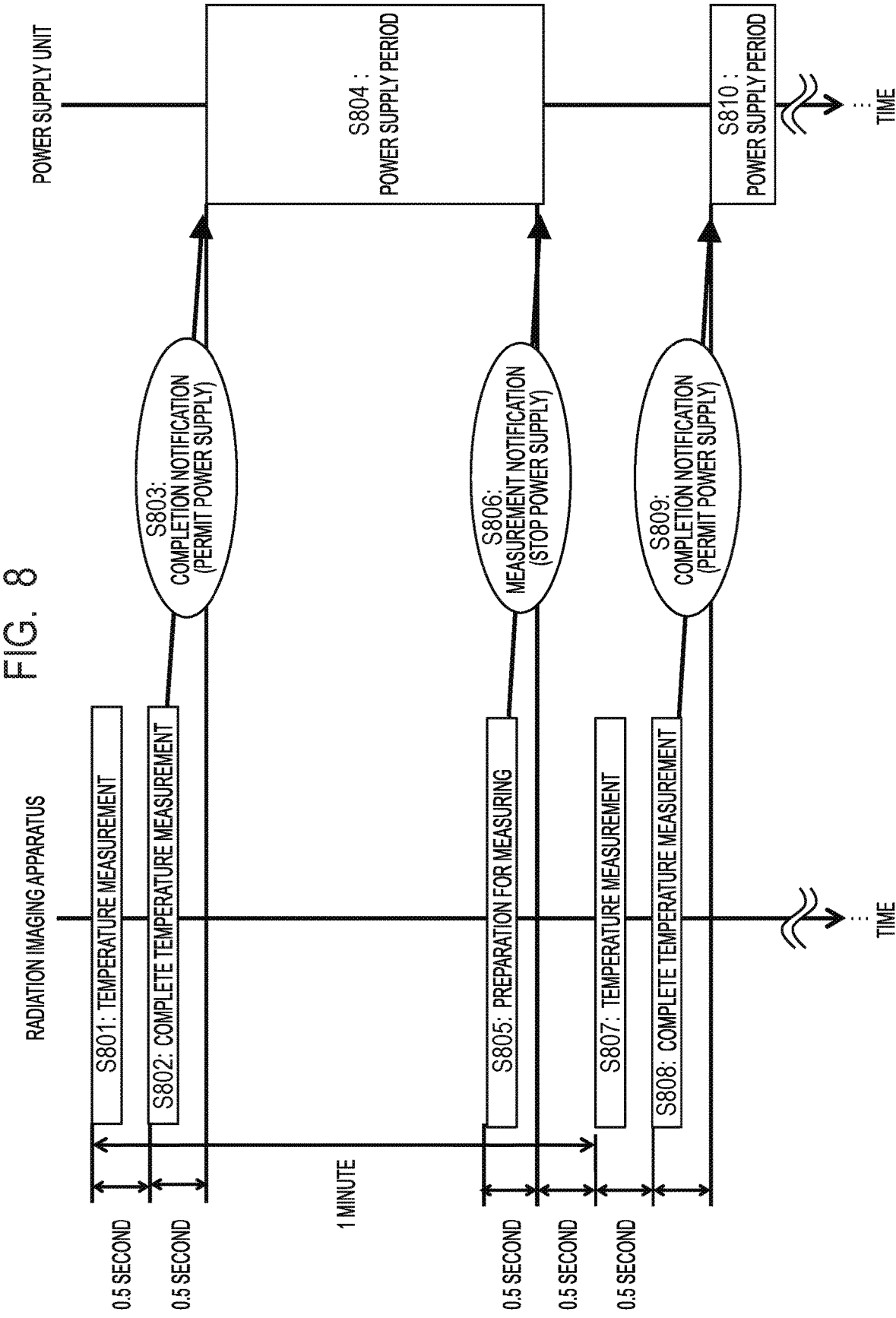
FIG. 8 is a flow chart for illustrating processing of permitting power supply and stopping power supply.

When it is assumed that the temperature measurement, extraction of data from the temperature sensor, and time it takes from when the radiation imaging apparatus 101 notifies the power supply unit 104 on the power transmission side to stop the power supply until when the power supply is actually stopped are each 0.5 second, processing as in FIG. 8 is considered.

After completion of the last temperature measurement (Step S801), the radiation imaging apparatus 101 completes the temperature measurement (Step S802). After a notification of completion is transmitted from the radiation imaging apparatus 101 to the power supply unit 104 (Step S803), the power supply unit 104 can start supplying power after 0.5 second at the latest. Thereafter, until the radiation imaging apparatus 101 issues a notification to stop the power supply, the power supply unit 104 continues the power supply in the power transmission period (Step S804). In this manner, the control unit 204 transmits, to the power supply unit (power supply unit) 104 which performs the non-contact power supply for the radiation imaging apparatus 101, information on the state (for example, start or stop of measurement or calibration) of the physical sensor unit 214.

When the next temperature measurement (Step S807) approaches, the radiation imaging apparatus 101 notifies the power supply unit 104, as a preparation for measuring (Step S805), a measurement notification (stop the power supply) (Step S806) one second in advance. In response, the power supply unit 104 stops the non-contact power supply. In the first embodiment, it is assumed that it takes 0.5 second to notify the stop of, and to stop, the non-contact power supply, and hence the power transmission by means of the non-contact power supply is stopped by 0.5 second before the actual temperature measurement (Step S807).

Thereafter, the temperature measurement (Step S807) is actually performed, and the radiation imaging apparatus 101 completes the temperature measurement by 0.5 second thereafter (Step S808). When the completion notification is transmitted from the radiation imaging apparatus 101 to the power supply unit 104 (Step S809), the power supply unit 104 continues the power supply in the power transmission period (Step S810). Subsequently, those processing steps are repeated.

Numerical values have been presented for each time as an example, but the time differs in practice depending on the physical sensor to be used and the application. Moreover, in the first embodiment, the description has been given on the premise that the physical sensor unit 214 is affected by the non-contact power supply, but the change in electromagnetic field caused by the non-contact power supply may not affect the physical sensor unit 214 in some cases because a relationship between positions of being actually mounted on the device is a separated one.

In the calibration of the physical sensor unit 214, repetitive processing as in the temperature measurement does not occur. As in the above-mentioned processing, before the instruction to calibrate is actually issued from the control unit 204 of the radiation imaging apparatus 101, the power supply unit 104 may be notified of calibration start information to stop the non-contact power supply.

According to the above-mentioned processing, the radiation imaging apparatus 101 can stop the non-contact power supply depending on its situation, and hence suppress the effect of the change in electromagnetic field caused by the non-contact power supply.

Second Embodiment

Now, a case in which a radiation imaging apparatus 101 including a power receiving function by means of contact power supply in addition to the functions of the radiation imaging apparatus 101 described in the first embodiment is used in conjunction with the power supply unit 104 is described.

Figure 9:
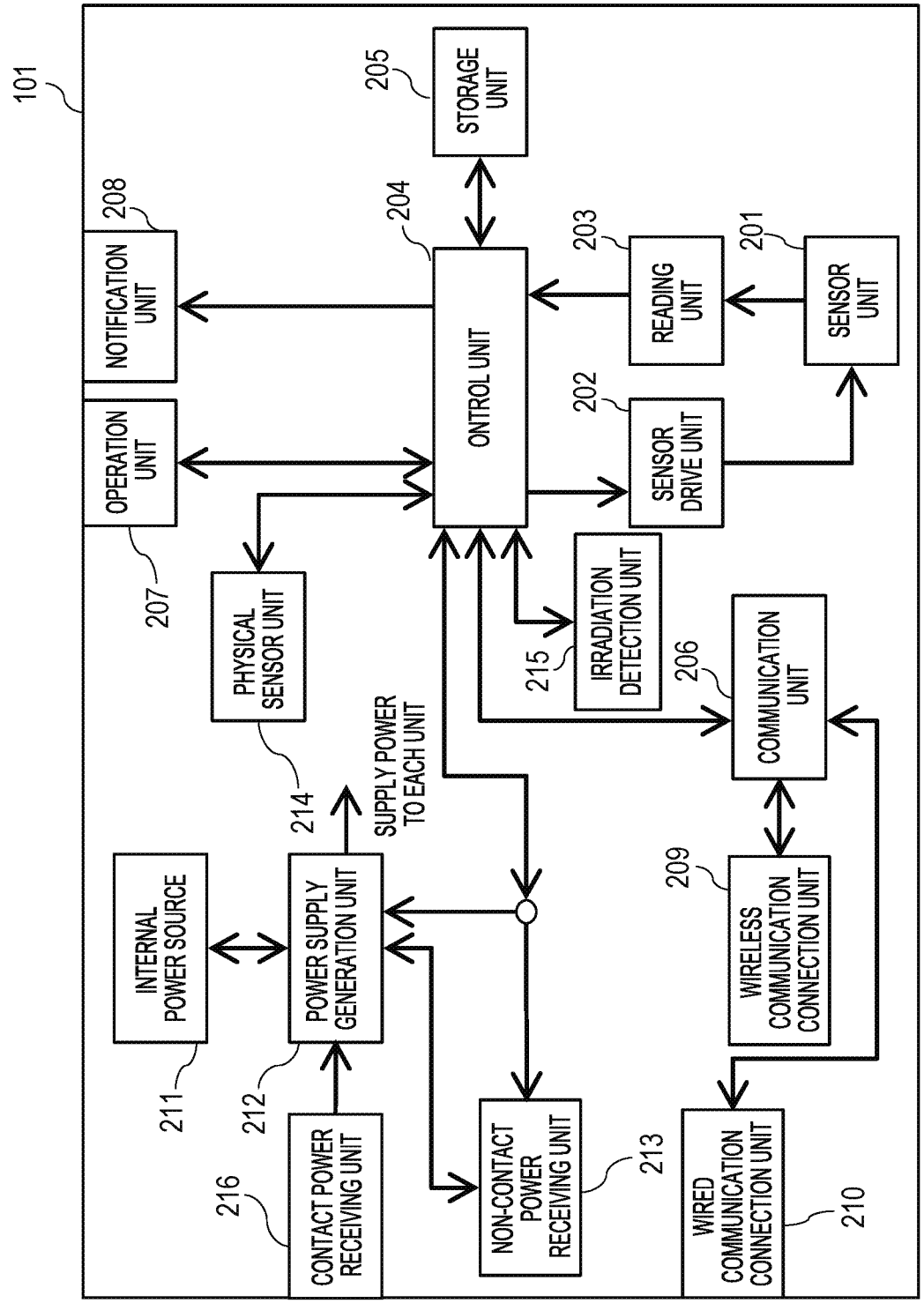
FIG. 9 is a diagram for illustrating a configuration example of a radiation imaging apparatus according to a second embodiment of the present invention.

In FIG. 9, a configuration example of the radiation imaging apparatus 101 discussed in a second embodiment of the present invention is illustrated. A contact power receiving unit 216 is added to the radiation imaging apparatus 101 of FIG. 2, which has been described in the first embodiment. As a result, the radiation imaging apparatus 101 can receive power in a contact manner. Further, the control unit 204 controls not only the non-contact power receiving unit 213 but also the power supply generation unit 212.

As a result, the radiation imaging apparatus 101 can receive both of the non-contact/contact power supply to increase safety in ensuring the power supply operation.

Figure 10:
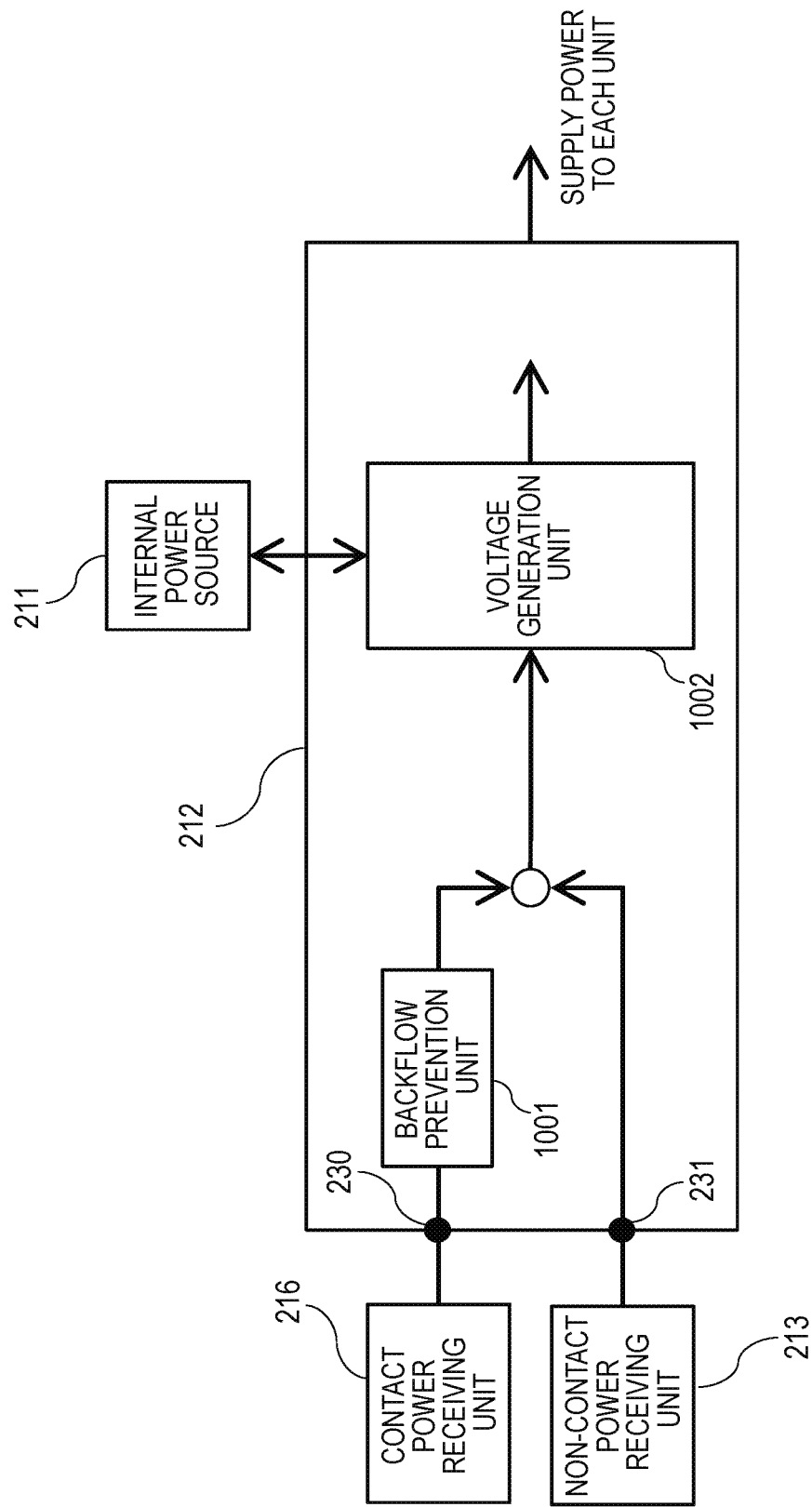
FIG. 10 is a diagram for illustrating a first configuration example of a power supply generation unit.

Moreover, with the power supply generation unit 212 being adapted to two inputs, the both power supply paths can be used at the same time to increase power that can be supplied at once. To that end, it is required that the power supply generation unit 212 be designed to allow both receiving voltages so as to receive power generated by means of both of the contact/non-contact power supply at one time, and that a mechanism configured to prevent the power by means of the non-contact power supply from flowing back to the contact power supply path be provided. An example of the power supply generation unit 212 in this case is illustrated in FIG. 10. For example, when a voltage applied to the contact power receiving unit 216 and a voltage output from the non-contact power receiving unit 213 are equal to each other, such configuration may be adopted.

In a case where the power supply is performed only by means of the non-contact power supply, when a connector for supplying power or the like is connected to the contact power receiving unit 216, the power received by means of the non-contact power receiving unit 213 may flow not to a voltage generation unit 1002 but to the contact power receiving unit 216. Therefore, a backflow prevention unit 1001 is required. In this example, the backflow prevention unit 1001 is provided only on the contact power receiving unit 216 side, but a backflow prevention function may be provided also on the non-contact power receiving unit 213 side to allow generation of a difference between a voltage from the contact power receiving unit 216 and a voltage from the non-contact power receiving unit 213 in an allowable input range of the voltage generation unit 1002.

Figure 11:
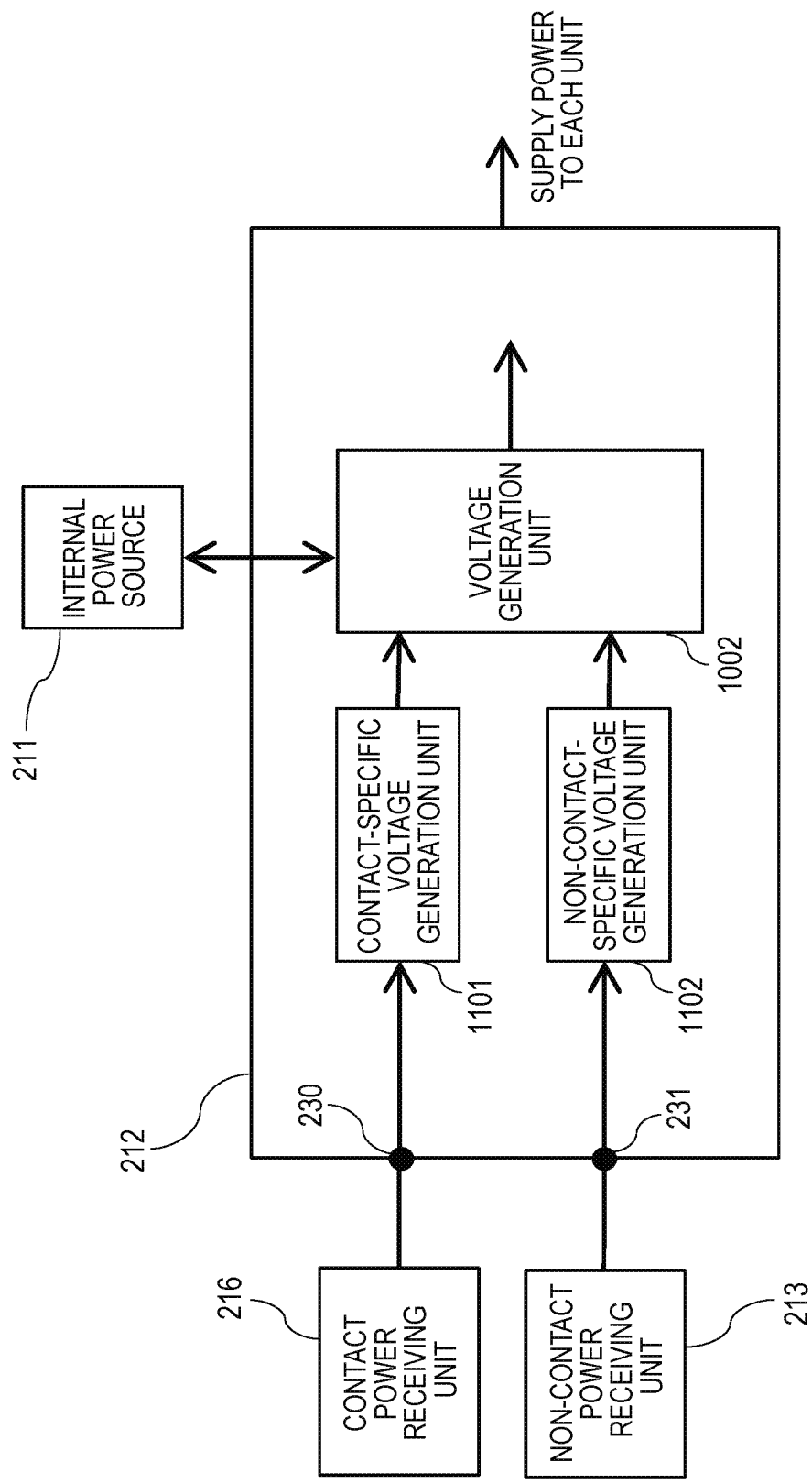
FIG. 11 is a diagram for illustrating a second configuration diagram of the power supply generation unit.

Alternatively, a mechanism in which contact/non-contact-specific input terminals 230 and 231 are provided to the power supply generation unit 212, and in which power from the input terminal 230 and power from the input terminal 231 are integrated on the output side, may be adopted. An example of the power supply generation unit 212 in this case is illustrated in FIG. 11. For example, the voltage applied to the contact power receiving unit 216 and the voltage output from the non-contact power receiving unit 213 may exceed the allowable input range of the voltage generation unit 1002 or generate a large difference therebetween in some cases. In those cases, it is required to change the voltages into voltages that can be used by the voltage generation unit 1002 with the above-mentioned configuration by interposing a contact-specific voltage generation unit 1101 and a non-contact-specific voltage generation unit 1102.

Further, in FIG. 12, the power supply unit 104 discussed in the second embodiment of the present invention is illustrated. A contact power transmission unit 311 is added to the power supply unit 104 which has been described in the first embodiment.

As a result, the power supply unit 104 can perform both of the non-contact/contact power supply. Through determining in advance the design of each power transmission unit and communication connection unit, the present invention can be adapted to any of the radiation imaging apparatus 101 having only the contact power supply function, the radiation imaging apparatus 101 having both of the contact/non-contact power supply functions, and the radiation imaging apparatus 101 having only the non-contact power supply.

Although illustration and description are omitted, it is possible to adopt a form in which, separately to the power supply unit 104 of FIG. 3 described in the first embodiment, a power supply unit 104 including a contact power transmission unit 311 may be prepared for power transmission.

Next, selection and processing as to whether or not to perform each of the contact power supply and the non-contact power supply are described.

First, a case in which both of the contact/non-contact power transmission serve as main power supply paths is described. In the second embodiment, it is assumed that the radiation imaging apparatus 101 and the power supply unit 104 illustrated in FIG. 9, FIG. 11, and FIG. 12 are used.

Under such a state, power can be transmitted and received both in the contact manner and in the non-contact manner, and hence, the power is basically received with the use of the both power supply paths. As a result, power transmission ability becomes larger than in the case where only one of them is used to supply power.

For the non-contact power supply, the effect of the electromagnetic field may be caused by the power supply, and hence stop processing similar to the processing details of the stop timing described in the first embodiment is required.

Further, without limiting to the non-contact power supply/contact power supply, any one of the power supply methods may be stopped at a timing that is different from the timing described in the first embodiment. For example, under a state in which power consumption of the radiation imaging apparatus 101 is low, and a charging rate of the internal power source 211 is high such that charging is affordable by small power, it is not required to use both of the non-contact/contact power transmission abilities. In that case, a method involving stopping an unnecessary power transmission path can be considered.

As to the power transmission path to be stopped, a method of selecting based on power transfer efficiency can be considered. Through acquisition or calculation of the power transfer efficiency as information from the supply side in advance or at a timing of determination, power can be selectively obtained from a power transmission path suited for the state (for example, power consumption) of the radiation imaging apparatus 101.

The control unit 204 stops, when the radiation apparatus 101 is in a state in which power consumed by the radiation imaging apparatus 101 can be supplied by at least one of the non-contact power reception and the contact power reception, one with lower power transfer efficiency of the non-contact power reception and the contact power reception. For example, when the contact power supply has higher transfer efficiency than that of the non-contact power supply, the power transmission by means of the non-contact power supply may be stopped at a timing at which the power consumption of the radiation imaging apparatus 101 becomes sufficiently affordable by the power supply from the power supply path by means of the contact power supply. A path along which information required for the stop is communicated is similar to that described in the first embodiment.

Alternatively, when the non-contact power supply has higher efficiency, the power supply by means of the contact power supply can be stopped at a similar timing. The case in which power transfer efficiency of the non-contact power supply is higher than power transfer efficiency of the contact power supply may occur when, as supplemented by the description of the power supply unit 104 in the second embodiment, a power supply unit 104 corresponding to the non-contact power supply and a power supply unit 104 corresponding to the contact power supply are separately prepared.

As an example, a case in which lengths of the power supply unit cables 302 of the power supply units 104 are different for each unit may be considered. When the power supply unit cable 302 of the power supply unit 104 adapted to the contact power supply exceeds a predetermined length, a resistance is increased, and hence a loss is increased, with the result that the power transfer efficiency is reduced.

As a method of stopping power supply through the contact power supply path, the control unit 204 may output a notification to stop to the power supply unit 104 via any one of the communication unit 206, the wireless communication connection unit 209, the wired communication connection unit 210, the AP 105, the communication network 103, and the power supply unit 104.

Further, it is possible to consider a method in which, as opposed to the non-contact power supply, instead of stopping the power supply on the power transmission side, the power reception is stopped on the radiation imaging apparatus 101 side. Specifically, there is a method of stopping, in the radiation imaging apparatus 101 including the power supply generation unit 212 as in FIG. 11, the power reception of the contact-specific voltage generation unit 1101.

As one specific implementation method, a switch is provided to an input of the contact-specific voltage generation unit 1101, and the switch is turned off to interrupt the electric current. When this method is performed, although the power supply unit 104 side supplies power to the contact power receiving unit 216 so as to perform the power supply, the contact-specific voltage generation unit 1101 does not receive the power, and hence the electric current is not allowed to flow. As a result, although a voltage appears at the contact power receiving unit 216, the electric current does not flow through the contact power receiving unit 216, with the result that no big loss is generated.

Next, a case in which any one of the contact/non-contact power supply paths serves as a main power supply path is described. In the second embodiment, it is assumed that the radiation imaging apparatus 101 and the power supply unit 104 illustrated in FIG. 9, FIG. 11, and FIG. 12 are used.

Under such a situation, when power can be supplied from the main power supply path, processing of giving a higher priority to the power supply from the path, and stopping the power supply from the subordinate power supply path may be performed. Further, if the main power supply path is of the non-contact power supply, it is required to perform processing of stopping the power supply described in the first embodiment. It is also possible to adopt a form in which the contact power supply is used in the period in which the non-contact power supply is stopped.

In order to achieve such a form, it is preferred for the radiation imaging apparatus 101 to determine which path is currently available for power supply, which path is currently used to receive the power supply, and the like.

For example, as to the function of determining the power reception, the contact power receiving unit 216 and the non-contact power receiving unit 213 may each have a power reception detection function, and transmit a determination result to the control unit 204 such that the radiation imaging apparatus 101 can determine the power receiving situation. Further, a function of determining whether the power supply generation unit 212 is receiving power is provided in the radiation imaging apparatus 101, and the control unit 204 is notified of a result of the determination such that the control unit 204 checks whether there is the non-contact power transmission unit 309 side via the non-contact power receiving unit 213 in response to the notification of the power reception. Then, when there is the non-contact power transmission unit 309, it may be determined that the non-contact power supply is performed. For the detection of the power reception, a plurality of kinds of means can be considered.

Further, as means for determining the path available for power supply, it is conceivable to employ a method involving checking that there is a corresponding power transmission unit side, and that communication can be performed to/from the power transmission side. For example, the control unit 204 checks whether the non-contact power transmission unit 309 or 404 is brought close to, or into contact with, the radiation imaging apparatus 101 through the communication function provided to the non-contact power receiving unit 213. The control unit 204 also checks whether the non-contact power transmission unit 309 or 404 that is brought close to, or into contact with, the radiation imaging apparatus 101 is connected to the power supply unit 104 that is in operation.

When the operating power supply unit 104 that is available for power supply responds with a communication response, the control unit 204 of the radiation imaging apparatus 101 determines to be in a state in which the non-contact power supply can be performed.

Further, for determining the contact power supply, similar processing may be performed via the wired communication connection unit 210 and the contact power transmission unit 311. The control unit 204 receives, from the power supply unit 104 which performs the non-contact power supply and the contact power supply for the radiation imaging apparatus 101, information on whether at least one of the non-contact power supply and the contact power supply is being performed.

With the above-mentioned processing, even when the radiation imaging apparatus 101 includes both of the non-contact/contact power supply paths, the non-contact power supply can be stopped depending on the status of the radiation imaging apparatus 101, and the effect of the change in electromagnetic field caused by the non-contact power supply can be suppressed. Further, power can be received through a preferred power supply path depending on the state of the radiation imaging apparatus 101.

Third Embodiment

Now, a case in which the radiation imaging apparatus 101 as described in the second embodiment is used while being connected to the cradle 113 described in the first embodiment is described.

For configurations, the radiation imaging apparatus 101 described in the first embodiment and the second embodiment, and the cradle 113 described in the first embodiment are referenced.

The radiation imaging apparatus 101 in the state of being connected to the cradle 113 does not assume imaging by radiation irradiation as described in the first embodiment. Therefore, a timing at which the radiation imaging apparatus 101 stops the non-contact power supply in order to prevent the effect of the non-contact power supply is assumed to be "in the detection operations of various physical sensors" described in the first embodiment.

In the cradle 113 illustrated in FIG. 5, the non-contact power transmission unit 404 can perform communication to/from an external device in addition to the power transmission as with the non-contact power transmission unit 309 of the power supply unit 104. Therefore, as in the method described in the first embodiment, the non-contact power supply can be stopped/started in consideration of the state of each radiation imaging apparatus 101.

As the timing to stop the non-contact power supply, a "read period for a correction image" is added. The "image read period" described in the first embodiment has been described to be a period required for the sensor drive unit 202 to select a read line and extract the electric charges accumulated in the sensor unit 201, and for the reading unit 203 to capture and digitize the electric charges. Then, there has been described the example in which there is the radiation imaging apparatus 101 which acquires the total of two images: the image of the offset information of the sensor array and the image after the radiation irradiation, to generate one image.

In the case of the radiation imaging apparatus 101 which acquires the two images to generate one image, the "image read period" required to acquire the images is the period in which the non-contact power supply is stopped.

In this example, the offset information for correction is acquired by imaging under a state in which the irradiation with the radiation is not performed. As one of the states in which the irradiation with the radiation is not performed, the situation in which the radiation imaging apparatus 101 is connected to the cradle 113 can be considered, and hence the offset information for correction is acquired in the period in which the radiation imaging apparatus 101 is connected to the cradle 113. When the imaging is performed by actually performing the irradiation with the radiation, it is possible to consider a method in which the radiation imaging apparatus 101 generates a final image with the use of the offset information that has been acquired in advance.

The period required to read the offset information is one of the "read period for a correction image", which is a timing to stop the non-contact power supply when the cradle 113 is used. The method and processing of stopping the non-contact power supply are similar to those "in the detection operations of various physical sensors" and in the "image read period" in the first embodiment. While the image of the offset information is taken, the radiation imaging apparatus 101 is in a state of acquiring an image without irradiation with radiation from the radiation generating apparatus 108 which generates the radiation, and the control unit 204 stops at least one of the non-contact power reception and the non-contact power supply of the radiation imaging apparatus 101.

In the third embodiment, the cradle 113 has been described above with reference to FIG. 5 in the first embodiment, but as with the power supply unit 104 described in the first embodiment and the second embodiment, the cradle 113 may include both of the non-contact/contact power supply mechanisms. As processing in that case, processing similar to that described in the second embodiment can be applied.

According to the above-mentioned processing, even when the radiation imaging apparatus 101 is connected to the cradle 113, the non-contact power supply can be stopped depending on the state of the radiation imaging apparatus 101, and the effect of the change in electric magnetic field caused by the non-contact power supply can be suppressed.

Fourth Embodiment

In the first to third embodiments, the power supply by means of the non-contact power supply is achieved by transmission and reception of power by being brought close to each other. In a fourth embodiment of the present invention, a case in which there is a non-contact power supply unit having a non-contact power supply function with which the power can be transmitted in a wide range to the power receiving mechanism is described mainly for parts that are different from the first embodiment to the third embodiment. A power transmission distance is varied depending on a mechanism and a configuration relating to power transmission, but in the fourth embodiment, the power transmission distance is described to allow power transmission over several meters, which is enough to cover an imaging room and a patient's room for radiation imaging.

First, in FIG. 13, an example of the radiation imaging system 100 including the radiation imaging apparatus 101 described in the fourth embodiment is illustrated. A non-contact power supply unit 114 is added to the configuration of FIG. 1.

The non-contact power supply unit 114 is communicably connected to the radiation imaging apparatus 101 via the communication network 103, for example, via wire or wirelessly. The non-contact power supply unit 114 can change the electromagnetic field in a predetermined range or more therearound or over a predetermined distance or more with directivity. The radiation imaging apparatus 101 on the power receiving side can receive power under the effect of the change in electromagnetic field.

Further, in FIG. 14, an example of an internal configuration of the non-contact power supply unit 114 is illustrated. The non-contact power supply unit 114 includes a power supply generation unit 1401 which receives power from an AC power source and converts the power into a DC voltage, an internal power supply unit 1402 which generates power to be used by each unit in the non-contact power supply unit 114, and a control unit 1403 which controls each unit.

The non-contact power supply unit 114 also includes a non-contact power transmission unit 1404 which performs non-contact power transmission, a communication unit 1405 which performs communication to/from an external device, and a wireless communication connection unit 1406 including an antenna for use in wireless communication, for example. The non-contact power supply unit 114 further includes a wired communication connection unit 1407, which is a connection unit for use in wired communication through a connector, for example.

Further, in FIG. 14, the configuration in which both of wireless/wired communication can be performed is illustrated, but a configuration having one of the communication functions may be adopted.

Further, in FIG. 13, the form in which the non-contact power supply unit 114 and the radiation imaging apparatus 101 are connected to each other via the communication network 103 is illustrated, but the non-contact power supply unit 114 and the radiation imaging apparatus 101 may be directly connected through wireless or wired connection.

The radiation imaging apparatus 101 is similar to that in the second embodiment except that the non-contact power receiving unit 213 has the mechanism in which power can be received in the predetermined range or more or over the predetermined distance or more from the non-contact power supply unit 114.

Further, as described in the first embodiment to the third embodiment, the power supply unit 104 and the cradle 113 in the fourth embodiment do not have the function of supplying power in a non-contact manner under a proximity state, but have the contact power supply function.

Next, the operation in the radiation imaging system 100 illustrated in FIG. 13, and the processing of starting/stopping the non-contact power supply are described.

The timing at which, and the period in which, the effect caused by the non-contact power supply is stopped are similar to those described in the first embodiment to the third embodiment. In other words, the non-contact power supply is stopped during the "image read period", "in the radiation irradiation detecting mode", "in the detection operations of various physical sensors", and in the "read period for a correction image".

As the path along which the instruction to start/stop the non-contact power supply is transmitted, the instruction is transmitted to the non-contact power supply unit 114 via the wireless communication connection unit 209 and the wired communication connection unit 210 included in the radiation imaging apparatus 101. As the units through which the instruction passes, the communication network 103, the AP 105, and other units are used, and a plurality of forms are applied as described above.

The non-contact power supply unit 114 receives the notification from the radiation imaging apparatus 101 by the communication unit 1405 via any one of the wireless communication connection unit 1406 and the wired communication connection unit 1407. Then, the non-contact power supply unit 114 stops the power supply by means of the non-contact power supply by the control unit 1403 controlling the output of the internal power supply unit 1402 or controlling the non-contact power transmission unit 1404 based on the notification, for example.

The radiation imaging apparatus 101 in the fourth embodiment includes the contact power receiving unit 216 separately from the non-contact power receiving unit 213, and hence can receive power by means of the contact power supply, and receive power by means of the non-contact power supply under the state of being connected to the non-contact power supply unit 114 and the cradle 113. The processing of transmitting the instruction to stop the power reception or to stop the power transmission under the state in which the power can be received by the two systems is similar to that described in the second embodiment.

A one-to-one relationship between the radiation imaging apparatus 101 and the non-contact power supply unit 114 has been described above, but a plurality of the radiation imaging apparatus 101 may receive power with respect to one non-contact power supply unit 114. In other words, the non-contact power supply unit 114 can perform the non-contact power supply for the plurality of radiation imaging apparatus 101. The control unit 1403 stops at least one of the non-contact power reception of and the non-contact power supply to a part or all of the plurality of radiation imaging apparatus 101 depending on the state of the radiation imaging apparatus 101.

The control unit 1403 stops at least one of the non-contact power reception of and the non-contact power supply to all of the plurality of radiation imaging apparatus 101 depending on the state of the radiation imaging apparatus 101 described in the first embodiment to the third embodiment. The stop processing is varied depending on what kind of power transmission mechanism is included in the non-contact power supply unit 114.

For example, when the non-contact power supply unit 114 transmits power in the predetermined range or more therearound, it is assumed that a plurality of radiation imaging apparatus 101-1, 101-2, and 101-3 are located in the power receivable range, and that the instruction to stop the power supply has been made from the radiation imaging apparatus 101-1. At this time, information on a reason for stopping the power supply to the radiation imaging apparatus 101-1 can be added to the instruction to stop the power supply. Then, it is determined whether to stop the power supply to the other radiation imaging apparatus 101-2 and 101-3 depending on the reason for stopping the power supply to the radiation imaging apparatus 101-1.

For example, when the reason for stopping the power supply is to prevent the effect on the image acquisition, it is determined that the stop time is a short time, and that the effect of not stopping the power supply is large, and the non-contact power supply unit 114 stops the power supply to the radiation imaging apparatus 101-2 and 101-3.

In contrast, when the reason for stopping the power supply is to stop the non-contact power supply because the power is sufficiently affordable by the contact power supply, it is determined that the stop time is a long time, and that the effect of not stopping the power supply is small, and the non-contact power supply unit 114 does not stop the power supply to the radiation imaging apparatus 101-2 and 101-3.

Further, when the non-contact power supply unit 114 includes a plurality of non-contact power transmission units with power transmission directivity, and when a power transmission area is shared by the non-contact power transmission units, one radiation imaging apparatus 101 may be arranged for each power transmission area of the non-contact power transmission unit, and the non-contact power supply may be started/stopped for each power transmission area.

For example, one radiation imaging apparatus 101 is generally arranged for each rack 111 or each bed 112 for imaging, which is arranged in a room for radiation imaging, and hence the rack 111 or the bed 112 having the radiation imaging apparatus 101 arranged therein may be arranged for each power transmission area. Moreover, when a plurality of radiation imaging apparatus 101 are arranged in the rack 111 or the bed 112 for long-length imaging of the object 110, the radiation imaging apparatus 101 are operated in conjunction with one another so as to transmit the request to stop the non-contact power supply to the plurality of radiation imaging apparatus 101 at the same time.

With the above-mentioned processing, even in the form in which the non-contact power supply is performed in the predetermined range or more or over the predetermined distance or more, the non-contact power supply can be stopped depending on the state of the radiation imaging apparatus 101, and hence the effect of the change in electromagnetic field caused by the non-contact power supply can be suppressed. Therefore, according to the first to fourth embodiments described above, the non-contact power supply can be performed appropriately depending on the state of the radiation imaging apparatus.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A radiation imaging apparatus, which is arranged to detect a radiation and receive a power in a non-contact manner, the radiation imaging apparatus comprising:
a control unit configured to stop at least one of a non-contact power reception of and a non-contact power supply to the radiation imaging apparatus depending on a state of the radiation imaging apparatus in a second period different from a first period during which radiation-based images are acquired.

2. The radiation imaging apparatus according to claim 1, further comprising:
a first sensor arranged to detect the radiation as electric charges to obtain the radiation-based images; and
a second sensor different from the first sensor,
wherein the control unit is configured to stop at least one of the non-contact power reception and the non-contact power supply depending on a state of the second sensor in the second period as the state of the radiation imaging apparatus in the second period.

3. The radiation imaging apparatus according to claim 2, wherein the control unit is configured to stop at least one of the non-contact power reception and the non-contact power supply if the radiation imaging apparatus is in a state of reading the electric charges from the first sensor.

4. The radiation imaging apparatus according to claim 3, wherein the control unit is configured to stop at least one of the non-contact power reception and the non-contact power supply if the first sensor is in a state of being calibrated.

5. The radiation imaging apparatus according to claim 3, wherein the control unit is configured to transmit, to a power supply arranged to perform the non-contact power supply, information on a state of the first sensor.

6. The radiation imaging apparatus according to claim 2, wherein the second sensor comprises a sensor for detecting an irradiation of the radiation from a radiation generator arranged to generate the radiation, and the second sensor is not used for generating the radiation-based image, and
wherein the control unit is configured to stop at least one of the non-contact power reception and the non-contact power supply in a response to a transition of the second sensor to a state in which the irradiation of the radiation is detectable.

7. The radiation imaging apparatus according to claim 2, wherein the second sensor comprises a sensor for detecting a predetermined physical quantity, and
wherein the control unit is configured to stop at least one of the non-contact power reception and the non-contact power supply if the second sensor is in a state in which the predetermined physical quantity is detectable.

8. The radiation imaging apparatus according to claim 2, wherein the second sensor comprises a sensor for detecting at least one of a temperature, a posture, and an acceleration of the radiation imaging apparatus, and
wherein the control unit is configured to stop at least one of the non-contact power reception and the non-contact power supply if the second sensor is in a state in which at least one of the temperature, the posture, and the acceleration of the radiation imaging apparatus is detectable.

9. The radiation imaging apparatus according to claim 1, wherein the control unit is configured to stop at least one of the non-contact power reception and the non-contact power supply if the radiation imaging apparatus is in a state of acquiring an image without an irradiation of the radiation from a radiation generator arranged to generate the radiation.

10. The radiation imaging apparatus according to claim 1, wherein the control unit is configured to transmit, to a power supply arranged to perform the non-contact power supply, information on a start or a stop of the non-contact power supply.

11. The radiation imaging apparatus according to claim 10, further comprising:
a power receiver configured to start the non-contact power reception by being brought close to the power supply arranged to perform the non-contact power supply,
wherein the power receiver is configured to transmit and receive the information to and from the power supply.

12. The radiation imaging apparatus according to claim 1, wherein the radiation imaging apparatus is further arranged to receive a power in a contact manner, and
wherein the control unit is configured to receive, from a power supply arranged to perform the non-contact power supply and a contact power supply for the radiation imaging apparatus, information on whether at least one of the non-contact power supply and the contact power supply is performed.

13. The radiation imaging apparatus according to claim 1, wherein the radiation imaging apparatus is further arranged to receive a power in a contact manner, and
wherein the control unit is configured to stop, if the radiation imaging apparatus is in a state in which a power consumed by the radiation imaging apparatus can be supplied by at least one of the non-contact power reception and a contact power reception, one with a lower power transfer efficiency of the non-contact power reception and the contact power reception.

14. A radiation imaging system comprising:
a plurality of radiation imaging apparatuses arranged to detect a radiation and receive a power in a non-contact manner;
a power supply arranged to perform a non-contact power supply for the plurality of radiation imaging apparatuses; and
a control unit configured to stop at least one of a non-contact power reception of and a non-contact power supply to a few or all of the plurality of radiation imaging apparatuses depending on a state of the plurality of radiation imaging apparatuses in a second period different from a first period during which radiation-based images are acquired by at least one of the plurality of radiation imaging apparatuses.

15. The radiation imaging system according to claim 14, wherein each radiation imaging apparatus of the plurality of the radiation imaging apparatuses comprises a first sensor arranged to detect the radiation as electric charges and a second sensor different from the first sensor,
wherein the control unit is configured to stop at least one of the non-contact power reception of and the non-contact power supply to the plurality of radiation imaging apparatuses under at least one of the following cases:
if the second sensor is in a state in which an irradiation of radiation from a radiation generator arranged to generate the radiation is detectable, in the second period; and
if the second sensor is in a state in which a predetermined physical quantity in at least one of the plurality of radiation imaging apparatuses is detectable, in the second period.

16. A radiation imaging method of taking a radiation image by a radiation imaging apparatus, which is arranged to take the radiation image, receiving a power in a non-contact manner, the radiation imaging method comprising:
a step of stopping at least one of a non-contact power reception of and a non-contact power supply to the radiation imaging apparatus depending on a state of the radiation imaging apparatus in a second period different from a first period during which radiation-based images are acquired.

17. A non-transitory computer-readable medium having stored thereon a program configured to cause, when executed by a processor, the processor to execute the step of the radiation imaging method of claim 16.

\* \* \* \* \*